(12) United States Patent
Xing et al.

(10) Patent No.: US 11,896,620 B2
(45) Date of Patent: Feb. 13, 2024

(54) ENGINEERED IMMUNE CELL AND USE THEREOF

(71) Applicant: NANJING BIOHENG BIOTECH CO., LTD, Jiangsu (CN)

(72) Inventors: Yun Xing, Jiangsu (CN); Zhonghui Yan, Jiangsu (CN); Ying Xiong, Jiangsu (CN); Rongrong Pu, Jiangsu (CN); Jiangtao Ren, Jiangsu (CN); Xiaohong He, Jiangsu (CN); Yanbin Wang, Jiangsu (CN); Lu Han, Jiangsu (CN)

(73) Assignee: BIOHENG THERAPEUTICS LIMITED, Grand Cayman (KY)

( * ) Notice: Subject to any disclaimer, the term of this patent is extended or adjusted under 35 U.S.C. 154(b) by 0 days.

(21) Appl. No.: 17/908,109

(22) PCT Filed: May 24, 2021

(86) PCT No.: PCT/CN2021/095556
§ 371 (c)(1),
(2) Date: Aug. 30, 2022

(87) PCT Pub. No.: WO2021/238877
PCT Pub. Date: Dec. 2, 2021

(65) Prior Publication Data
US 2023/0138756 A1 May 4, 2023

(30) Foreign Application Priority Data

May 27, 2020 (CN) .......................... 202010460730.5
Jun. 16, 2020 (CN) .......................... 202010550754.X

(51) Int. Cl.
A61K 35/17 (2015.01)
C07K 14/725 (2006.01)
A61K 39/00 (2006.01)

(52) U.S. Cl.
CPC .......... *A61K 35/17* (2013.01); *C07K 14/7051* (2013.01); *A61K 2039/5156* (2013.01); *C07K 2317/70* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 10,751,422 | B2 | 8/2020 | Rudra et al. |
| 2014/0228794 | A1 | 8/2014 | Bonnefin et al. |
| 2018/0021253 | A1 | 1/2018 | Sandeep et al. |
| 2018/0037657 | A1 | 2/2018 | Rudra et al. |
| 2020/0071679 | A1 | 3/2020 | Huang et al. |
| 2020/0109364 | A1* | 4/2020 | DiPersio ............. C12N 5/0636 |

FOREIGN PATENT DOCUMENTS

| | | |
|---|---|---|
| CN | 108064176 A | 5/2018 |
| CN | 108472346 A | 8/2018 |
| CN | 108866003 A | 11/2018 |
| CN | 109153989 A | 1/2019 |
| CN | 110101723 A | 8/2019 |
| CN | 110964122 A | 4/2020 |
| CN | 111163758 A | 5/2020 |
| CN | 111729084 A | 10/2020 |
| CN | 111849910 A | 10/2020 |
| CN | 111849913 A | 10/2020 |
| JP | 2007295852 A | 11/2007 |
| WO | 2010040362 A1 | 4/2010 |
| WO | 2011/162821 A1 | 12/2011 |
| WO | 2017100403 A1 | 6/2017 |
| WO | 2020000035 A1 | 1/2020 |
| WO | 2020028656 A1 | 2/2020 |
| WO | 2020/045610 A1 | 3/2020 |
| WO | 2020068261 A1 | 4/2020 |
| WO | 2020252303 A1 | 12/2020 |
| WO | 2021233317 A1 | 11/2021 |
| WO | 2022223049 A1 | 10/2022 |

OTHER PUBLICATIONS

Poirot, L. et al., Cancer Res., 2015: pp. 3853-3864.*
Lai, J. et al., Nat. Immunol., vol. 21: Epub May 18, 2020; pp. 914-926.*
Adachi, K. et al, Nat. Biotech, Apr. 2018, Supplementary Material; 27 pages.*
Heng, "Debating cancer: The paradox in cancer research", World Scientific Publishing Co. Pte. Ltd: Singapore. 2015. 464. ISBN 978-981-4520-84-3, pp. 1-6.
English Abstract of Heng, "Debating cancer: The paradox in cancer research" retrieved on https://www.ncbi.nlm.nih.gov/pmc/articles/PMC5793485/ on Feb. 2, 2023, 3 pages.
Office Action with regard to the CA Patent Application No. 3,169,656 dated Dec. 22, 2022.
Adachi et al., "IL-7 and CCL19 expression in CAR-T cells improves immune cell infiltration and CAR-T cell survival in the tumor", Nature Biotechology, 2018, vol. 36, No. 4, pp. 346-353.
Sánchez-Paulete et al., "Intratumoral Immunotherapy with XCL1 and sFlt3L Encoded in Recombinant Semliki Forest Virus-Derived Vectors Fosters Dendritic Cell-Mediated T-cell Cross-Priming", Cancer Research, 2018, vol. 78, No. 23, pp. 6643-6654.
European Search Report with regard to the counterpart EP Patent Application No. 21813383 completed Jun. 26, 2023.
Office Action with regard to the corresponding JP Patent Application No. 2022-552469 dated Aug. 16, 2023.
De Andrade et al., "Discovery of specialized NK cell populations infiltrating human melanoma metastases", JCI Insight, 2019, vol. 4, No. 23, pp. 1-12.

(Continued)

*Primary Examiner* — Michael D Burkhart
(74) *Attorney, Agent, or Firm* — BCF LLP

(57) ABSTRACT

An engineered immune cell, which expresses (i) a cell surface molecule that specifically recognizes a ligand, (ii) an exogenous interleukin, and (iii) an exogenous Flt3L, XCL2, and/or XCL1; the engineered immune cell can be used for treating cancer, infection, or autoimmune diseases; and compared with a traditional engineered immune cell, the engineered immune cell has significantly improved tumor killing activity.

22 Claims, 9 Drawing Sheets
Specification includes a Sequence Listing.

(56) References Cited

OTHER PUBLICATIONS

European Communication with regard to the counterpart EP Patent Application No. 21813383 dated Jul. 17, 2023.
English Abstract for JP2007295852 retreived on Espacenet on Aug. 31, 2023.
Huynh, "Effect of Chemokine/Cytokine Delivered by Nanoparticles on Tumor Migration of Neuroblastoma Targeting Chimeric Antigen Receptor T Cells", Non-Viral Gene Transfer and Therapy II, Molecular Therapy, vol. 24, Supplement 1, 2016, p. S236.
International Search Report and Written Opinion (and English Translation of ISR) with regard to PCT/CN2021/095556 dated Aug. 27, 2021.
Office Action 1 (and English Translation) with regard to CN Patent Application No. 202010550754.X dated Dec. 15, 2020.
Office Action 2 (and English Translation) with regard to CN Patent Application No. 202010550754.X dated Feb. 23, 2021.
Notification of Grant (and English Translation) with regard to CN Patent Application No. 202010550754.X.
English Abstract for CN108064176 retrieved on Espacenet on Aug. 30, 2022.
English Abstract for CN108472346 retrieved on Espacenet on Aug. 30, 2022.
English Abstract for CN108866003 retrieved on Espacenet on Aug. 30, 2022.
English Abstract for CN109153989 retrieved on Espacenet on Aug. 30, 2022.
English Abstract for CN110101723 retrieved on Espacenet on Aug. 30, 2022.
English Abstract for CN110964122 retrieved on Espacenet on Aug. 30, 2022.
English Abstract for CN111163758 retrieved on Espacenet on Aug. 30, 2022.
English Abstract for CN111729084 retrieved on Espacenet on Aug. 30, 2022.
English Abstract for CN111849910 retrieved on Espacenet on Aug. 30, 2022.
English Abstract for CN111849913 retrieved on Espacenet on Aug. 30, 2022.

* cited by examiner

ENGINEERED IMMUNE CELL AND USE THEREOF

CROSS-REFERENCE TO RELATED APPLICATIONS

This application is a national phase filing under 35 U.S.C. 371 of International Application No. PCT/CN2021/095556 filed on May 24, 2021, which claims the benefit of Chinese Patent Application No. 202010360730.5, filed on May 27, 2020, and of Chinese Patent Application No. 202010550754.X, filed on Jun. 16, 2020. The contents of the aforementioned applications are incorporated by reference in their entirety herein.

Electronic File—Sequence Listing

This application contains an electronic Sequence Listing which has been submitted in ASCII format via EFS-WEB and is hereby incorporated by reference in its entirety. The material in the electronic Sequence Listing is submitted as a text (.txt) file entitled "OP122171041CNUS-corrected-sequence-listing" created on Jan. 18, 2023, and has a file size of 65,174 byte.

TECHNICAL FIELD

The present disclosure belongs to the field of immunotherapy. More specifically, the present disclosure relates to an engineered immune cell, which expresses (i) a cell surface molecule that specifically recognizes a ligand, (ii) an exogenous interleukin, and (iii) an exogenous Flt3L, XCL2, and/or XCL1 gene. More preferably, the cell surface molecule that specifically recognizes a ligand is a chimeric antigen receptor.

BACKGROUND ART

Tumor immunotherapy mainly eliminates tumor cells by regulating the human immune system and tumor microenvironment, and finally relying on autoimmunity. The immune system is a unified whole, and innate immunity also plays a quite important role in tumor immunity.

Some antigen presenting cells, such as dendritic cells and macrophages, are bridges connecting innate immunity and acquired immunity. The antigen presenting cells can recognize a tumor antigen and present the same to the acquired immune system, activate tumor specific T cells, thereby eliminating the tumor. Therefore, increasing the tumor killing effect of the immune system by enhancing the antigen presentation process is an important research direction of tumor immunity.

CAR cell therapy is an important tumor cell immunotherapy. Successful control of tumor by CAR cell generally requires following several processes: immune system activation, activation and amplification of CAR cell, infiltration of activated CAR cell into the tumor tissue to kill the tumor cell. However, there is a general problem with the current CAR cell therapy, i.e., the tumor microenvironment has an inhibitory effect on the CAR cell, such that the CAR cell cannot infiltrate the tumor tissue. Therefore, how to reduce the inhibitory effect of the tumor microenvironment on CAR cell, improve survival time of CAR cell, or recruit other immune cells to act synergistically with CAR cell is quite important for improving the therapeutic effect of CAR cell.

It has been reported that interleukin IL-7 and chemokine CCL-19 recruit endogenous dendritic cells into the tumor tissue, activate tumor-reactive endogenous T cell and differentiate the same into memory T cells, so as to promote the anti-tumor activity of conventional TCR-T cell (see CN109153989A) or CAR-T cell (Adachi, K., Kano, Y., Nagai, T. et al. IL-7 and CCL19 expression in CAR-T cells improves immune cell infiltration and CAR-T cell survival in the tumor. Nat Biotechnol 36, 346-351 (2018)).

Conventional type 1 dendritic cell (conventional DC1, cDC 1) is a subset of dendritic cells, and is a main immune cell presenting the tumor antigens. Research results show that cDC1 can effectively present tumor-associated antigens, particularly necrotic cell-associated antigens, effectively induce antigen-specific CD8+ T cell response, and play an extremely important role in the in-vivo tumor killing process. Both mouse and human studies show that the distribution of cDC1 in the tumor microenvironment is positively correlated with the anti-tumor immune response, and thus is an important evaluation parameter of tumor-related immune score. The cDC1 is less distributed in mice and humans, and is almost invisible in the tumor microenvironment of mouse and human with a low tumor immune response rate. Optimizing the role of cDC1 in tumor therapy is an important direction of research for improving the tumor immunotherapy effect.

CCL-19 has the ability to recruit dendritic cells and endogenous T cells into tumors, but it has a limited ability to recruit cDC1 dendritic cells, therefore, there is a need for a new immunotherapeutic approach that can effectively differentiate or recruit cDC1 dendritic cells, so as to improve tumor antigen presentation efficiency, induce the body's adoptive immune response, solve the problem of tumor heterogeneity, thus improving the efficacy of CAR cell therapy.

SUMMARY

In a first aspect, the present disclosure provides a novel engineered immune cell, which expresses (i) a cell surface molecule that specifically recognizes a ligand, (ii) an exogenous interleukin, and (iii) an exogenous Flt3L, XCL2, and/or XCL1 gene.

In an embodiment, the cell surface molecule that specifically recognizes a ligand is a chimeric antigen receptor or a T cell receptor, preferably, a chimeric antigen receptor.

In an embodiment, the interleukin is IL-2, IL-7, IL-12, IL-15, IL-21, IL-17, IL-18, IL-23, or a subunit thereof, or a combination thereof, or a combination of subunits thereof, preferably IL-7.

In an embodiment, the interleukin, Flt3L, XCL2, or XCL1 protein is a fusion protein or mutant that is resistant to proteolysis.

In an embodiment, the immune cell is selected from the group consisting of a T cell, a macrophage, a dendritic cell, a monocyte, an NK cell, or an NKT cell. Preferably, the T cell is a CD4+/CD8+ T cell, a CD4+ helper T cell, a CD8+ T cell, a tumor infiltrating cell, a memory T cell, a naive T cell, a γδ-T cell, or a αβ-T cell.

In an embodiment, the cell surface molecule that specifically recognizes a ligand is a chimeric antigen receptor, which contains a ligand binding domain, a transmembrane domain, a co-stimulatory domain, and an intracellular signaling domain. In the above, the ligand binding domain may be selected from the group consisting of scFv, Fab, single domain antibody, nanobody, antigen binding ligand, recombinant fibronectin domain, anticalin, and DARPIN. Preferably, the ligand binding domain is selected from the group consisting of scFv, Fab, single domain antibody, and nanobody.

In an embodiment, the cell surface molecule that specifically recognizes a ligand binds to a target selected from the group consisting of: TSHR, CD19, CD123, CD22, BAFF-R, CD30, CD171, CS-1, CLL-1, CD33, CD171, CS-1, CLL-1, CD33, EGFRvIII, GD2, GD3, BCMA, GPRCSD, Tn Ag, PSMA, ROR1, FLT3, FAP, TAG72, CD38, CD44v6, CEA, EPCAM, B7H3, KIT, IL-13Ra2, mesothelin, IL-11Ra, PSCA, PRSS21, VEGFR2, LewisY, CD24, PDGFR-β, SSEA-4, CD20, AFP, Folate receptor α, ERBB2 (Her2/neu), MUC1, EGFR, CS1, CD138, NCAM, Claudin18.2, Prostase, PAP, ELF2M, Ephrin B2, IGF-I receptor, CAIX, LMP2, gp100, bcr-ab1, tyrosinase, EphA2, Fucosyl GM1, sLe, GM3, TGS5, HMW-MAA, o-acetyl-GD2, Folate receptor β, TEM1/CD248, TEM7R, CLDN6, GPRCSD, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, NKG2D, and any combination thereof. Preferably, the target is selected from the group consisting of: CD19, CD20, CD22, CD30, CD33, CD38, CD123, CD138, CD171, MUC1, AFP, Folate receptor α, CEA, PSCA, PSMA, Her2, EGFR, IL13Ra2, GD2, NKG2D, EGFRvIII, CS1, BCMA, mesothelin, and any combination thereof.

In an embodiment, the transmembrane domain is a transmembrane domain of a protein selected from the group consisting of: TCR α chain, TCR β chain, TCR γ chain, TCR δ chain, CD3 ζ subunit, CD3 ε subunit, CD3 γ subunit, CD3 δ subunit, CD45, CD4, CD5, CD8 α, CD9, CD16, CD22, CD33, CD28, CD37, CD64, CD80, CD86, CD134, CD137, and CD154. Preferably, the transmembrane domain is selected from a transmembrane domain of CD8 α, CD4, CD28, and CD278.

In an embodiment, the intracellular signaling domain is a signaling domain of a protein selected from the group consisting of: FcR γ, FcR β, CD3 γ, CD3 δ, CD3 ε, CD3 ζ, CD22, CD79a, CD79b, and CD66d. Preferably, the intracellular signaling domain is a signaling domain containing CD3 ζ.

In an embodiment, the co-stimulatory domain is one or more co-stimulatory signaling domains of a protein selected from the group consisting of: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM), CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, ZAP70, and a combination thereof. Preferably, the co-stimulatory domain is a co-stimulatory signaling domain of CD27, CD28, CD134, CD137 or CD278 or a combination thereof.

In an embodiment, the expression or activity of the exogenous interleukin, Flt3L, XCL2 and/or XCL1 is constitutive expression. In another embodiment, the expression or activity of the exogenous interleukin, Flt3L, XCL2 and/or XCL1 is conditional expression. For example, the conditional expression is achieved by operably linking the exogenous genes to an inducible, repressible or tissue-specific promoter.

In an embodiment, the interleukin, Flt3L, XCL2, and/or XCL1 may be operably linked to a localization domain, wherein the localization domain can locate the exogenous gene of the present disclosure at a specific cellular position for expression, for example, a cell membrane, a specific organelle in the cytoplasm, e.g., endoplasmic reticulum, golgi apparatus, nucleus, etc. The localization domain includes, but is not limited to, a nuclear localization signal, a leader peptide, a transmembrane domain, and the like. In an embodiment, the exogenous genes, i.e., interleukin, Flt3L, XCL2, and/or XCL1 of the present disclosure are operably linked to the transmembrane domain, so as to be anchored on the surface of the engineered immune cell to be expressed.

In a second aspect, the present disclosure provides a nucleic acid molecule, containing (i) a nucleic acid sequence encoding a cell surface molecule that specifically recognizes a ligand, (ii) a nucleic acid sequence encoding an interleukin, and (iii) a nucleic acid sequence encoding Flt3L, XCL2, and/or XCL1. Preferably, the cell surface molecule that specifically recognizes a ligand is a chimeric antigen receptor or a T cell receptor, more preferably a chimeric antigen receptor. Preferably, the interleukin is IL-2, IL-7, IL-12, IL-15, IL-21, IL-17, IL-18, IL-23, or a subunit thereof, or a combination thereof, or a combination of subunits thereof, more preferably IL-7, a subunit thereof, or a combination thereof. Preferably, the nucleic acid is DNA or RNA.

The present disclosure further provides a vector containing the above nucleic acid molecule. Specifically, the vector is selected from the group consisting of plasmid, retrovirus, lentivirus, adenovirus, vaccinia virus, Rous Sarcoma Virus (RSV), polyoma virus, and adeno-associated virus (AAV). In some embodiments, the vector further contains elements such as an origin autonomously replicating in an immune cell, a selectable marker, a restriction enzyme cleavage site, a promoter, a poly-A tail (polyA), 3' UTR, 5' UTR, an enhancer, a terminator, an insulator, an operon, a selectable marker, a reporter gene, a targeting sequence, and/or a protein purification tag. In a specific embodiment, the vector is an in vitro transcription vector.

In an embodiment, the present disclosure further provides a kit, which contains the engineered immune cell, the nucleic acid molecule, or the vector of the present disclosure.

In an embodiment, the present disclosure further provides a pharmaceutical composition, which contains the engineered immune cell, the nucleic acid molecule, or the vector of the present disclosure, and one or more pharmaceutically acceptable excipients.

In a third aspect, the present disclosure further provides a method of preparing an engineered immune cell, including introducing the following into the immune cell: (a) a first nucleic acid sequence encoding a cell surface molecule that specifically recognizes a ligand or the cell surface molecule that specifically recognizes a ligand encoded thereby; (b) a second nucleic acid sequence encoding interleukin or interleukin encoded thereby; and (c) a third nucleic acid sequence encoding XCL1, XCL2, and/or Flt3L or XCL1, XCL2, and/or Flt3L protein encoded thereby. Preferably, the cell surface molecule that specifically recognizes a ligand is a chimeric antigen receptor or a chimeric T cell receptor, more preferably a chimeric antigen receptor. Preferably, the interleukin is IL-2, IL-7, IL-12, IL-15, IL-21, IL-17, IL-18, IL-23, or a subunit thereof, or a combination thereof, or a combination of subunits thereof, more preferably IL-7, a subunit thereof, or a combination of subunits thereof.

In an embodiment, the above components (a), (b), and (c) can be introduced in sequence into the immune cell in any order. In another embodiment, the above components (a), (b), and (c) can be simultaneously introduced into the immune cell, e.g., cloning (a), (b), and (c) in one or more vectors.

In a fourth aspect, the present disclosure further provides a method of treating a subject with cancer, infection or autoimmune disease, including administering to the subject an effective amount of the immune cell, the nucleic acid molecule, the vector or the pharmaceutical composition according to the present disclosure.

In an embodiment, the cancer is a solid tumor or a hematologic tumor. More specifically, the cancer is selected from the group consisting of: brain glioma, blastoma, sarcoma, leukemia, basal cell carcinoma, biliary tract cancer, bladder cancer, bone cancer, brain and CNS cancer, breast cancer, peritoneal cancer, cervical cancer, choriocarcinoma, colon and rectal cancer, connective tissue cancer, cancer of digestive system, endometrial cancer, esophageal cancer, eye cancer, head and neck cancer, stomach cancer, glioblastoma (GBM), liver cancer, hepatoma, intraepithelial tumor, kidney cancer, larynx cancer, liver tumor, lung cancer, lymphoma, melanoma, myeloma, neuroblastoma, oral cancer, ovarian cancer, pancreatic cancer, prostate cancer, retinoblastoma, rhabdomyosarcoma, rectal cancer, cancer of respiratory system, salivary gland cancer, skin cancer, squamous cell carcinoma, stomach cancer, testicular cancer, thyroid cancer, uterine or endometrial cancer, malignant tumor of urinary system, vulval cancer and other cancers and sarcomas, and B cell lymphoma, mantle cell lymphoma, AIDS-related lymphoma, and Waldenstrom macroglobulinemia, chronic lymphocytic leukemia (CLL), acute lymphocytic leukemia (ALL), B cell acute lymphocytic leukemia (B-ALL), T cell acute lymphocytic leukemia (T-ALL), B cell prolymphocytic leukemia, blast cell plasmacytoid dendritic cell tumor, Burkitt lymphoma, diffuse large B cell lymphoma, follicular lymphoma, chronic myelogenous leukemia (CML), malignant lymphoproliferative disorder, MALT lymphoma, hairy cell leukemia, marginal zone lymphoma, multiple myeloma, myelodysplasia, plasmablastic lymphoma, preleukemia, plasmacytoid dendritic cell tumor, and post-transplant lymphoproliferative disorder (PTLD).

In an embodiment, the infection includes, but is not limited to, infections caused by viruses, bacteria, fungi, and parasites.

In an embodiment, the autoimmune disease includes, but is not limited to, type I diabetes, celiac disease, Graves disease, inflammatory bowel disease, multiple sclerosis, psoriasis, rheumatoid arthritis, Addison disease, sicca syndrome, Hashimoto thyroiditis, myasthenia gravis, vasculitis, pernicious anemia, and systemic lupus erythematosus, etc.

The advantages of the engineered immune cell of the present disclosure lie in that the co-expressed interleukin and Flt3L, XCL2, and/or XCL1 can effectively promote the differentiation or recruitment of DC cells at the tumor site, increase the number of DC cells, and increase the proliferation and survival time of engineered immune cell, thus, on one hand, reducing the inhibitory effect of the tumor microenvironment on the engineered immune cell, and improving the tumor killing ability of the engineered immune cell, and on the other hand, the increased DC cells can activate the adoptive immune recognition of the body's own T cells, which forms synergistic effect with the engineered immune cell, and eventually enhances the inhibition for tumor.

DETAILED DESCRIPTION OF EMBODIMENTS

Figure 1:
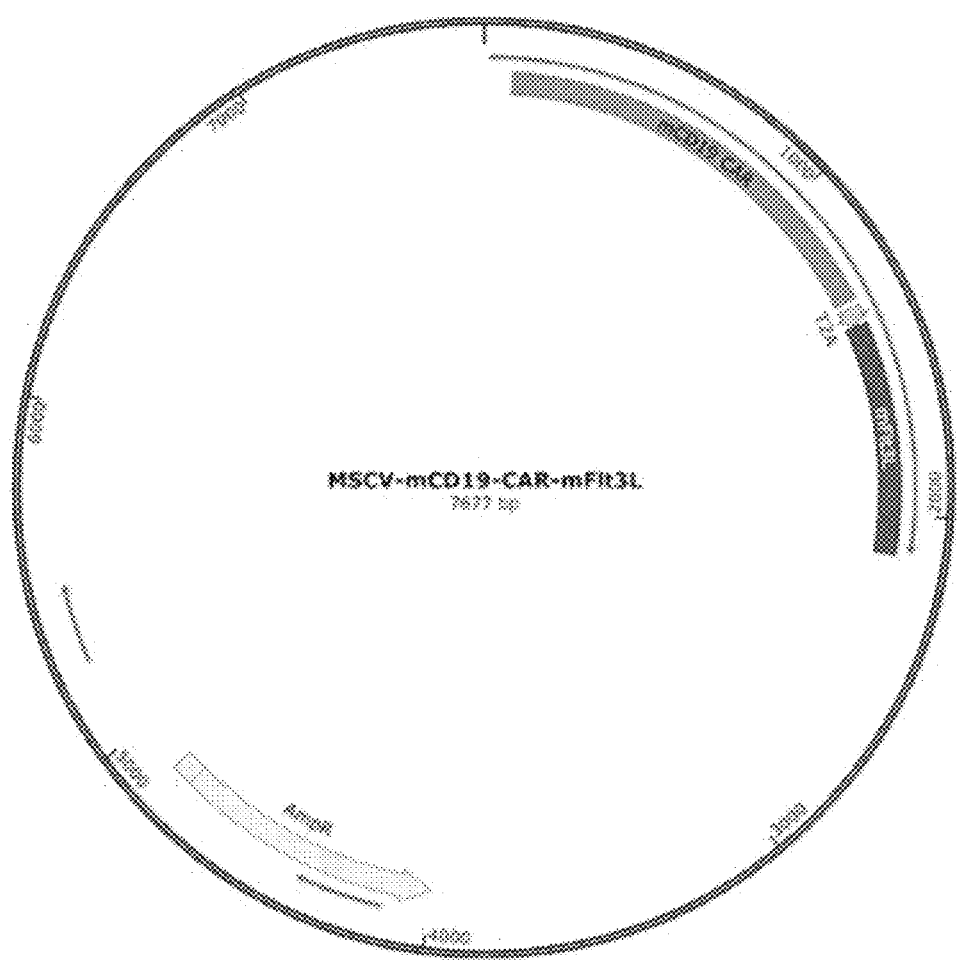
FIG. 1: structural schematic view of recombinant retroviral vector mCD19-CAR-Flt3L.
Figure 2:
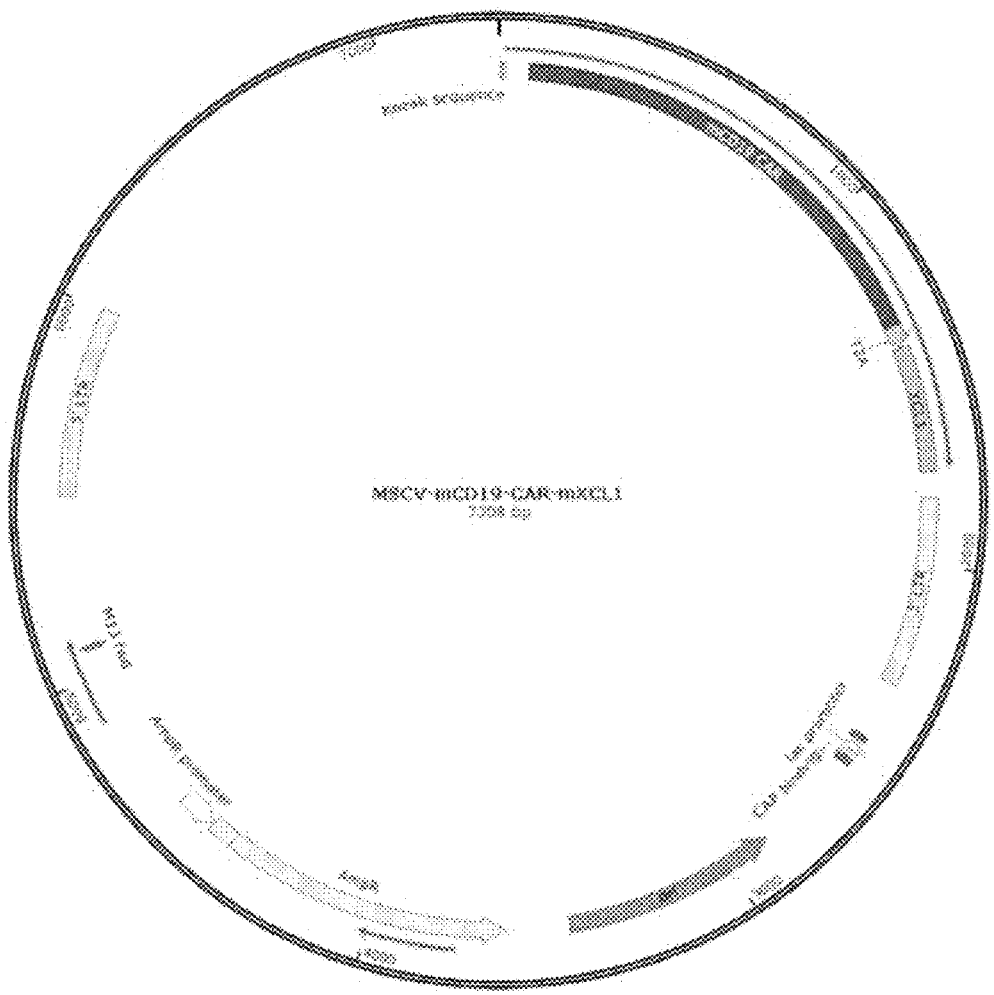
FIG. 2: structural schematic view of recombinant retroviral vector mCD19-CAR-XCL1.

Unless otherwise indicated, all scientific and technical terms used herein have the same meaning as commonly understood by one of ordinary skill in the art to which the present disclosure belongs.

Cell Surface Molecule that Specifically Recognizes a Ligand

As used herein, the term "cell surface molecule that specifically recognizes a ligand" refers to a molecule expressed on a cell surface and being capable of specifically binding to a target molecule (e.g., ligand). Such surface molecule generally contains a ligand binding domain capable of specifically binding to a ligand, a transmembrane domain anchoring the surface molecule to the cell surface, and an intracellular domain responsible for signaling. Examples of such common surface molecules include, for example, T cell receptor or chimeric antigen receptor.

As used herein, the term "T cell receptor" or "TCR", refers to a membrane protein complex that responds to antigen presentation and participates in T cell activation. Stimulation of TCR is triggered by major histocompatibility complex molecules (MHC) on antigen presenting cells, which present antigen peptides to T cells and bind the same to TCR complexes so as to induce a series of intracellular signaling. TCR is composed of six peptide chains forming heterodimers respectively, and is generally sorted into αβ type and γδ type. Each peptide chain includes a constant region and a variable region, wherein the variable region is responsible for binding to specific antigens and MHC molecules. The variable region of TCR may contain a ligand binding domain or is operably linked to a ligand binding domain, wherein the ligand binding domain is defined as follows.

As used herein, the term "chimeric antigen receptor" or "CAR" refers to an artificially constructed hybrid polypeptide, where the hybrid polypeptide generally includes a ligand binding domain (e.g., an antigen binding portion of an antibody), a transmembrane domain, a co-stimulatory domain, and an intracellular signaling domain, and various domains are linked via a linker. CAR can redirect the specificity and reactivity of T cell and other immune cells to a selected target in a non-MHC-restricted manner by utilizing the antigen binding properties of monoclonal antibodies. Non-MHC-restricted antigen recognition gives CAR cell the ability to recognize an antigen independent of antigen processing, thus bypassing the major mechanism of tumor escape. Besides, when expressed within T cell, CAR advantageously does not dimerize with α chain and β chain of the endogenous T cell receptor (TCR).

As used herein, "ligand binding domain" refers to any structure or functional variant thereof that can bind to a ligand (e.g. antigen). The ligand binding domain may be an antibody structure, including, but not limited to, monoclonal antibody, polyclonal antibody, recombinant antibody, human antibody, humanized antibody, murine antibody, chimeric antibody, and functional fragment thereof. For example, the ligand binding domain includes, but is not limited to, Fab, Fab', Fv fragment, F(ab')2, single chain antibody fragment (scFv), single domain antibody (sdAb), nanobody (Nb), antigen binding ligand, recombinant fibronectin domain, anticalin, DARPIN, and so on, preferably selected from Fab, scFv, sdAb, and nanobody. In the present disclosure, the ligand binding domain may be monovalent or bivalent, and may be a monospecific, bispecific or multispecific antibody. In another embodiment, the ligand binding domain also may be a specific binding polypeptide or receptor of a specific protein, wherein the specific protein is, for example, PD1, PDL1, PDL2, TGFβ, APRIL, and NKG2D.

"Fab" refers to any one of two identical fragments produced after an immunoglobulin molecule is cleaved by papain, and consists of an intact light chain and a heavy chain N-terminal part linked by a disulfide bond, wherein the heavy chain N-terminal part includes a heavy chain variable region and CH1. Compared with intact IgG, Fab has no Fc fragment, has relatively high fluidity and tissue penetration ability, and can univalently bind to an antigen without mediating antibody effects.

"Single chain antibody" or "scFv" is an antibody composed of antibody's heavy chain variable region (VH) and light chain variable region (VL) linked by a linker. The optimal length and/or amino acid composition of the linker can be selected. The length of the linker will significantly affect the variable region folding and interaction of the scFv. In fact, intrachain folding can be prevented if a shorter linker (e.g. 5-10 amino acids) is used. Regarding the selection of size and composition of the linker, see, e.g., Hollinger et al., 1993 Proc Natl Acad. Sci. U.S.A. 90:6444-6448; US patent applications with publication Nos. 2005/0100543, 2005/0175606, 2007/0014794; and PCT applications with publication Nos. WO2006/020258 and WO2007/024715, which are incorporated herein by reference in their entirety. The scFv may contain a VH and a VL linked in any order, e.g., VH-linker-VL or VL-linker-VH.

"Single domain antibody" or "sdAb" refers to an antibody that naturally lacks light chain, and the antibody contains only one heavy chain variable region (VHH) and two conventional CH2 and CH3 regions, also known as "heavy chain antibody".

"Nanobody" or "Nb" refers to a VHH structure that is individually cloned and expressed, which has structural stability and binding activity to an antigen comparable to those of the original heavy chain antibody, and is the smallest unit currently known to be capable of binding to a target antigen.

The term "functional variant" or "functional fragment" refers to a variant that substantially includes the amino acid sequence of a parent, but, compared with the parent amino acid sequence, contains at least one amino acid modification (i.e., substitution, deletion, or insertion), provided that the variant retains the biological activity of the parent amino acid sequence. In one embodiment, the amino acid modification is preferably a conservative modification.

As used herein, the term "conservative modification" refers to amino acid modification that does not significantly affect or alter the binding characteristics of the antibody or antibody fragment containing the amino acid sequence. These conservative modifications include amino acid substitution, addition, and deletion. The modifications can be introduced into the chimeric antigen receptor of the present disclosure by standard techniques known in the art, such as site-directed mutagenesis and PCR-mediated mutagenesis. The conservative amino acid substitution is a substitution in which the amino acid residue is replaced with an amino acid residue having a similar side chain. Amino acid residue families having a similar side chain have been defined in the art, including basic side chain (e.g., lysine, arginine, histidine), acidic side chain (e.g., aspartic acid, glutamic acid), uncharged polar side chain (e.g., glycine, asparagine, glutamine, serine, threonine, tyrosine, cysteine), nonpolar side chain (e.g., alanine, valine, leucine, isoleucine, proline, phenylalanine, methionine, tryptophan), β-branched side chain (e.g., threonine, valine, isoleucine), and aromatic side chain (e.g., tyrosine, phenylalanine, tryptophan, histidine). The conservative modifications may be selected, for example, based on polarity, charge, solubility, hydrophobicity, hydrophilicity, and/or similarity in amphiphilic properties of residues involved.

Thus, the "functional variant" or "functional fragment" has at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the parent amino acid sequence, and retains the biological activity, e.g., binding activity, of the parent amino acid.

As used herein, the term "sequence identity" indicates the degree to which two (nucleotide or amino acid) sequences have the same residue at the same position in an alignment, and is generally expressed by percentage. Preferably, the identity is determined over the entire length of the sequences being compared. Thus, two copies with completely identical sequences have 100% identity. Those skilled in the art will recognize that some algorithms can be used to determine sequence identity using standard parameters, for example, Blast (Altschul et al. (1997) Nucleic Acids Res. 25:3389-3402), Blast2 (Altschul et al. (1990) J. Mol. Biol. 215:403-410), Smith-Waterman (Smith et al. (1981) J. Mol. Biol. 147:195-197), and ClustalW.

The selection of ligand binding domain depends on the cell surface marker on a target cell to be recognized and associated with a specific disease state, for example, a tumor specific antigen or a tumor associated antigen. Thus, in an embodiment, the ligand binding domain of the present disclosure binds to one or more targets selected from the group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, mesothelin, IL-11Ra, PSCA, PRSS21, VEGFR2, LewisY, CD24, PDGFR-β, SSEA-4, CD20, Folate receptor α, ERBB2 (Her2/neu), MUC1, EGFR, NCAM, Prostase, PAP, ELF2M, Ephrin B2, IGF-I receptor, CAIX, LMP2, gp100, bcr-ab1, tyrosinase, EphA2, Fucosyl GM1, sLe, GM3, TGS5, HMW-MAA, o-acetyl-GD2, Folate receptor β, TEM1/CD248, TEM7R, CLDN6, GPRCSD, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, NKG2D, and any combination thereof. Preferably, the target is selected from the group consisting of: CD19, CD20, CD22, BAFF-R, CD33, EGFRvIII, BCMA, GPRCSD, PSMA, ROR1, FAP, ERBB2 (Her2/neu), MUC1, EGFR, CAIX, WT1, NY-ESO-1, CD79a, CD79b, GPC3, Claudin18.2, NKG2D, and any combination thereof. Depending on the antigen to be targeted, the CAR of the present disclosure may be designed to include a ligand binding domain specific for the antigen. For example, if CD19 is the antigen to be targeted, a CD19 antibody can be used as a ligand binding domain of the present disclosure. In a preferred embodiment, the CAR of the present disclosure contains a CD19 scFv, which contains a light chain variable region sequence having at least 90%, 95%, 97% or 99% or 100% sequence identity to an amino acid sequence depicted in sites 1-107 of SEQ ID NO: 2 or sites 1-107 of SEQ ID NO: 14 and a heavy chain variable region sequence having at least 90%, 95%, 97% or 99% or 100% sequence identity to an amino acid sequence depicted in sites 123-242 of SEQ ID NO: 2 or sites 123-238 of SEQ ID NO: 14.

As used herein, the term "transmembrane domain" refers to a polypeptide structure that enables expression of a chimeric antigen receptor on the surface of an immune cell (e.g., a lymphocyte, an NK cell, or an NKT cell), and guides a cellular response of the immune cell against the target cell. The transmembrane domain may be natural or synthetic, and also may be derived from any membrane-bound protein or transmembrane protein. The transmembrane domain is capable of signaling when the chimeric antigen receptor binds to the target antigen. The transmembrane domains particularly suitable for use in the present disclosure may be derived from, for example, a TCR α chain, a TCR β chain, a TCR γ chain, a TCR δ chain, a CD3 ζ subunit, a CD3 ε subunit, a CD3 γ subunit, a CD3 δ subunit, CD45, CD4, CD5, CD8 α, CD9, CD16, CD22, CD33, CD28, CD37, CD64, CD80, CD86, CD134, CD137, CD154, and functional fragments thereof. Alternatively, the transmembrane domain may be synthesized and may mainly contain a hydrophobic residue such as leucine and valine. Preferably, the transmembrane domain is derived from a CD8 α chain, which has at least 70%, preferably at least 80%, more preferably at least 90%, 95%, 97% or 99% or 100% sequence identity to an amino acid sequence represented by SEQ ID NO: 4 or 16, or an encoding sequence of the CD8 α transmembrane domain has at least 70%, preferably at least 80%, more preferably at least 90%, 95%, 97% or 99% or 100% sequence identity to a nucleotide sequence represented by SEQ ID NO: 3 or 15.

In an embodiment, the chimeric antigen receptor of the present disclosure further may contain a hinge region located between the ligand binding domain and the transmembrane domain. As used herein, the term "hinge region" generally refers to any oligopeptide or polypeptide that functions to link a transmembrane domain to a ligand binding domain. Specifically, the hinge region serves to provide greater flexibility and accessibility to the ligand binding domain. The hinge region may contain up to 300 amino acids, preferably 10 to 100 amino acids and most preferably 25 to 50 amino acids. The hinge region may be completely or partially derived from a natural molecule, for example, completely or partially from the extracellular region of CD8, CD4 or CD28, or completely or partially from an antibody constant region. Alternatively, the hinge region may be a synthetic sequence corresponding to a naturally occurring hinge sequence, or may be a completely synthetic hinge sequence. In a preferred embodiment, the hinge region contains a hinge region portion of a CD8 α chain, an Fc γ RIII a receptor, an IgG4, or an IgG1, more preferably a CD8 α hinge, which has at least 70%, preferably at least 80%, more preferably at least 90%, 95%, 97% or 99% or 100% sequence identity to an amino acid sequence represented by SEQ ID NO: 12 or 22, or an encoding sequence of the CD8 α hinge has at least 70%, preferably at least 80%, more preferably at least 90%, 95%, 97% or 99% or 100% sequence identity to a nucleotide sequence represented by SEQ ID NO: 11 or 21.

As used herein, the term "intracellular signaling domain" refers to a protein portion that transduces an effector function signal and guides a cell to perform a specified function. The intracellular signaling domain is responsible for intracellular primary signaling after the ligand binding domain binds to the antigen, thus causing activation of immune cell and immune reaction. In other words, the intracellular signaling domain is responsible for activating at least one of the normal effector functions of the immune cells in which the CAR is expressed. For example, the effector functions of T cell can be cytolytic activity or auxiliary activity, including secretion of cytokines.

In an embodiment, the intracellular signaling domain contained in the chimeric antigen receptor of the present disclosure may be cytoplasmic sequences of a T cell receptor and a co-receptor, upon antigen receptor binding, which act together to initiate primary signaling, as well as any derivative or variant of these sequences and any synthetic sequence having the same or similar function. The intracellular signaling domain may contain many immunoreceptor tyrosine-based activation motifs (ITAM). Non-limiting examples of intracellular signaling domain of the present disclosure include, but are not limited to, those derived from FcR γ, FcR β, CD3 γ, CD3 δ, CD3 ε, CD3 ζ, CD22, CD79a, CD79b, and CD66d. In a preferred embodiment, the signaling domain of the CAR of the present disclosure may contain a CD3 ζ signaling domain, and the signaling domain has at least 70%, preferably at least 80%, more preferably at least 90%, 95%, 97%, or 99% or 100% sequence identity to an amino acid sequence represented by SEQ ID NO: 8 or 20, or an encoding sequence thereof has at least 70%, preferably at least 80%, more preferably at least 90%, 95%, 97%, or 99% or 100% sequence identity to a nucleotide sequence represented by SEQ ID NO: 7 or 19.

In an embodiment, the chimeric antigen receptor of the present disclosure contains one or more co-stimulatory domains. The co-stimulatory domain may be an intracellular functional signaling domain from a co-stimulatory molecule, which contains an entire intracellular portion of the co-stimulatory molecule, or a functional fragment thereof "Co-stimulatory molecule" refers to a homologous binding partner that specifically binds to a co-stimulatory ligand on a T cell, thereby mediating a co-stimulatory response (e.g. proliferation) of the T cell. The co-stimulatory molecule includes, but is not limited to, MHC class 1 molecules, BTLA, and Toll ligand receptors. Non-limiting examples of the co-stimulatory domain of the present disclosure include, but are not limited to, co-stimulatory signaling domains derived from a protein selected from the group consisting of: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM), CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, and ZAP70. Preferably, the co-stimulatory domain of the CAR of the present disclosure is from 4-1BB, CD28, CD27, OX40, or a combination thereof. In an embodiment, the co-stimulatory domain contained in the CAR of the present disclosure has at least 70%, preferably at least 80%, more preferably at least 90%, 95%, 97%, or 99% or 100% sequence identity to an amino acid sequence represented by SEQ ID NO: 6 or 18, or an encoding sequence of the co-stimulatory domain has at least 70%, preferably at least 80%, more preferably at least 90%, 95%, 97%, or 99% or 100% sequence identity to a nucleotide sequence represented by SEQ ID NO: 5 or 17.

In an embodiment, the CAR of the present disclosure further may contain a signal peptide such that when it is expressed in a cell such as a T cell, the nascent protein is directed to the endoplasmic reticulum and subsequently to the cell surface. The core of the signal peptide may contain a long hydrophobic amino acid segment, which has a tendency to form a single α-helix. At the end of the signal peptide, there is usually an amino acid segment recognized and cleaved by signal peptidase. The signal peptidase can cleave during or after translocation, so as to generate free signal peptide and mature protein. Then, the free signal peptide is digested by a specific protease. Signal peptides that can be used in the present disclosure are well known to those skilled in the art, for example, signal peptides derived from CD8 α, IgG1, GM-CSFRα, and so on. In an embodiment, the signal peptide that can be used in the present disclosure has at least 70%, preferably at least 80%, more preferably at least 90%, 95%, 97%, or 99% or 100% sequence identity to an amino acid sequence represented by SEQ ID NO: 10 or 34, or an encoding sequence of the signal peptide has at least 70%, preferably at least 80%, more preferably at least 90%, 95%, 97%, or 99% or 100% sequence identity to a nucleotide sequence represented by SEQ ID NO: 9 or 33.

In an embodiment, the CAR of the present disclosure further may contain a switch structure to regulate the expression time of the CAR. For example, the switch structure may be in a form of dimerization domain, which causes a conformational change by binding to a corresponding ligand thereof, and exposes the extracellular binding domain to enable its binding to a targeted antigen, thereby activating a signaling pathway. Alternatively, a switch domain also may be used to link the binding domain and signaling domain, respectively, and only when the switch domains are bound to each other (for example, in the presence of an inducing compound), the binding domain and the signaling domain can be linked together through a dimer, thereby activating signaling pathway. The switch structure also can be in the form of a masking peptide. The masking peptide can shield the extracellular binding domain, and prevent it from binding to the targeted antigen. When the masking peptide is cleaved by, for example, a protease, the extracellular binding domain is exposed, making it become a "normal" CAR structure. A variety of switch structures known to those skilled in the art can be used in the present disclosure.

In an embodiment, the CAR of the present disclosure further may contain a suicide gene, to make it express a cell death signal that can be induced by an exogenous substance, so as to eliminate the CAR cell when needed (e.g., when serious toxic side effects are produced). For example, the suicide gene may be in the form of an inserted epitope, e.g., a CD20 epitope, an RQR8, etc., and when needed, the CAR cell can be eliminated by adding an antibody or reagent that targets these epitopes. The suicide gene also may be herpes simplex virus thymidine kinase (HSV-TK), which gene can induce the cell to die when receiving ganciclovir treatment. The suicide gene further may be iCaspase-9, and dimerization of iCaspase-9 can be induced by a chemical induction drug such as AP1903 and AP20187, so as to activate the downstream Caspase3 molecule, and cause apoptosis. A variety of suicide genes known to those of skill in the art can be used in the present disclosure.

In an embodiment, the chimeric antigen receptor contains: (a) a 4-1BB co-stimulatory domain and a CD3 ζ intracellular signaling domain, (b) a CD27 co-stimulatory domain and a CD3 ζ intracellular signaling domain, (c) a CD28 co-stimulatory domain and a CD3 ζ intracellular signaling domain, (d) an OX40 co-stimulatory domain and a CD3 ζ intracellular signaling domain, (e) a CD28 co-stimulatory domain, a 4-1BB co-stimulatory domain, and a CD3 ζ intracellular signaling domain, (f) an OX40 co-stimulatory domain, a 4-1BB co-stimulatory domain, and a CD3 ζ intracellular signaling domain, or (g) a CD28 co-stimulatory domain, an OX40 co-stimulatory domain, and a CD3 ζ intracellular signaling domain.

Interleukin

Interleukins are a class of cytokines produced by leukocytes and functioning between leukocytes, and play an important role in transmitting information, activating and regulating immune cells, mediating T and B cell activation, proliferation, and differentiation, and inflammatory reactions. Basically, the biological effects of interleukins are achieved by their binding to corresponding receptor, e.g., the biological properties of IL-7 are achieved by the binding of IL-7 to its receptor IL-7R.

In an embodiment, the interleukins that can be used in the present disclosure include, but are not limited to, IL-2, IL-7, IL-12, IL-15, IL-21, IL-17, IL-18, IL-23, or a subunit thereof, or a combination thereof, or a combination of subunits thereof. IL-2 is mainly produced by T cells and function by autocrine and paracrine. IL-2 not only can maintain T cell growth, promote the production of cytokines, but also can induce CD8+ T cells and CD4+ T cells to exert cytotoxic effect. In addition, IL-2 also can stimulate NK cell to proliferate, enhance the NK killing activity, promote the NK cells to produce factors such as IFNγ, TNFβ, and TGFβ. IL-2 can also activate macrophages, and enhance the antigen presenting ability and the target cell killing ability of the macrophages. IL-7 is mainly produced by bone marrow and thymic stromal cells, and its main functions relate to the following aspects: promoting precursor B cell growth; inhibiting peripheral T cell apoptosis, inducing cell proliferation, and sustained survival; and affecting the development and function of dendritic cells and macrophages, and inducing macrophages to secrete multiple cytokines. IL-12 mainly acts on T cells and NK cells. Specifically, IL-12 can stimulate proliferation of activated T cells, and promote differentiation of Th0 cells to Th1 cells; induce cytotoxic activities of CTL and NK cells and promote the same to secrete cytokines such as IFNγ, TNFα, and GMCSF; and promote expression of NK cells and IL-2Ra, TNF receptors, and CD56, and enhance an ADCC effect on tumor cells. IL-15 can be produced by a variety of cells, such as activated macrophages, epidermal cells, and fibroblasts. As the molecular structure of IL-15 is similar to that of IL-2, it can bind to target cells by using the β chain and γ chain of IL-2R, and exert a biological activity similar to that of IL-2, for example, stimulating proliferation of T cells and NK cells, and inducing proliferation and differentiation of B cells. IL-21 is produced by activated CD4+ T cells, NKT cells, Tfh cells, and Th17 cells, and has high homology with IL-2 and IL-15. IL-21 has a wide range of immunomodulatory functions. Its activation can enhance proliferation of activated CD8+ T cells, enhance the cytotoxic activity of NK cells, and promote proliferation and differentiation of B cells. IL-17 is secreted by Th17 cells, and is a proinflammatory molecule. It can inhibit regulatory T cells, and recruit and activate neutrophils and macrophages. IL-18 is also a proinflammatory molecule and is secreted by T cells and NK cells. Activated macrophages also secrete a large amount of IL-18. It has been reported that IL-18 plays an important role in innate immunity and adoptive immunity. IL-23 is likewise secreted by T cells and NK cells, and IL-23 can promote Th17 cell differentiation. Dendritic cells, monocytes, and macrophages also express IL-23 receptors at a low-level, and can be activated by IL-23. Studies have shown that these interleukins, alone or in combination, can exert effective anti-tumor effects.

In an embodiment, the interleukin used in the present disclosure has at least 70%, preferably at least 80%, more preferably at least 90%, 95%, 97%, or 99% or 100% sequence identity to an amino acid sequence represented by SEQ ID NO: 23, 27, 39, 41, 43, 45, 47, 49, 51, 53, 55, 57 or 59, or an encoding sequence thereof has at least 70%, preferably at least 80%, more preferably at least 90%, 95%, 97%, or 99% or 100% sequence identity to a nucleic acid sequence represented by SEQ ID NO: 24, 28, 40, 42, 44, 46, 48, 50, 52, 54, 56, 58 or 60.

Flt3L Gene

Tyrosine kinase receptor 3 ligand (Fms-like tyrosine kinase 3 ligand, Flt3L) is a cytokine, and it can specifically bind to an Fms-like tyrosine kinase 3 receptor (Flt3R), thereby promoting proliferation, differentiation, and maturation of DC cells, natural killer cells, cytotoxic T lymphocytes, etc. Flt3L is widely found in tissues and organs of human and mouse. Flt3L is expressed the most in monocytes of human peripheral blood, secondly in heart, placenta, lung, spleen, thymus, ovary, small intestine, liver, kidney, and pancreas, and the least in brain tissues.

Studies show that Flt3L can promote T cell proliferation with cytokines, such as IL-6, IL-7, and IL-13. In addition, Flt3L has an important influence on early differentiation of B cells, and differentiation of blood-derived precursor cells such as NK cells and DCs. In particular, Flt3L can selectively amplify DC precursor cells to promote differentiation of DCs since only premature DCs can express the receptor Flt3R. Studies have shown that subcutaneous injection of Flt3L into mice can significantly increase the number of DCs in their lymphatic and non-lymphatic tissues. It has been reported that the combined use of recombinant adenoviral vectors carrying Flt3L and chemotherapeutic drug 5-fluorouracil achieves significant anti-tumor effects in mouse models with liver cancer or rectal cancer. Specifically, by stimulating proliferation and differentiation of bone marrow immune cells, Flt3L effectively prevents the bone marrow injury caused by chemotherapeutic drugs, while DCs locally proliferated in tumor effectively present fragments of tumor cells killed by 5-fluorouracil and NK cells, thereby stimulating a specific anti-tumor immune response.

In an embodiment, the Flt3L used in the present disclosure has at least 70%, preferably at least 80%, more preferably at least 90%, 95%, 97%, or 99% or 100% sequence identity to an amino acid sequence represented by SEQ ID NO: 36 or 38, or an encoding sequence of Flt3L has at least 70%, preferably at least 80%, more preferably at least 90%, 95%, 97%, or 99% or 100% sequence identity to a nucleic acid sequence represented by SEQ ID NO: 35 or 37.

XCL1 and XCL2 Genes

The C-type chemokine family, also known as lymphotactin, includes two members, XCL1 and XCL2, mainly produced by CD8+ T cells and natural killer cells. XCL1 has unique sequence features and two protein space conformations switchable to each other, so that XCL1 is different from other chemokines and exerts unique functions. The XCL1-specific receptor XCR1 is a member of a G-protein coupled receptor family, and the interaction of the two not only plays an important role in the negative selection of thymus and the establishment of autoimmune tolerance, but also can initiate cross antigen presentation and mediate a cytotoxic immune response. The XCL1 not only can regulate the balance of immune system, and maintain the intestinal immune homeostasis, but also is associated with various diseases, such as autoimmune diseases, nephritis, tuberculosis, and human immunodeficiency virus infections. The nucleic acid sequences of XCL2 and XCL1 have 97% identity, wherein two amino acid residues at sites 7 and 8 are different: Asp and Lys in XCL1, and His and Arg in XCL2. It is found that XCL2 and XCL1 are quite similar in expression profile, structure, and function, for example, like XCL1, XCL2 also has two interconvertible protein space conformations, i.e., haplotype and dimeric type, wherein the haplotype conformation binds to and activates XCR1, and the dimeric-type conformation has higher affinity to a hairpin structure in glycosaminoglycan (GAG). The receptor XCR1 of XCL1 and XCL2 is selectively expressed on a DC (cDC1) cell having an antigen presenting ability, and it is found that introducing XCL1 can effectively improve the therapeutic effects of anti-tumor immunotherapy and a target vaccine.

In an embodiment, the XCL1 used in the present disclosure has at least 70%, preferably at least 80%, and more preferably at least 90%, 95%, 97% or 99% or 100% sequence identity to an amino acid sequence represented by SEQ ID NO: 26 or 30, or an encoding sequence of XCL1 has at least 70%, preferably at least 80%, and more preferably at least 90%, 95%, 97% or 99% or 100% sequence identity to a nucleic acid sequence represented by SEQ ID NO: 25 or 29.

In an embodiment, the XCL2 used in the present disclosure has at least 70%, preferably at least 80%, and more preferably at least 90%, 95%, 97% or 99% or 100% sequence identity to an amino acid sequence represented by SEQ ID NO: 68, or an encoding sequence of XCL2 has at least 70%, preferably at least 80%, and more preferably at least 90%, 95%, 97% or 99% or 100% sequence identity to a nucleic acid sequence represented by SEQ ID NO: 67.

Expression of Exogenous Gene

Expression of the exogenous gene in the present disclosure, e.g., interleukin, Flt3L, XCL2, and/or XCL1, can be constitutive expression or conditional expression.

In an embodiment, the expression of the exogenous interleukin, Flt3L, XCL2, and/or XCL1 is conditional expression. For example, the exogenous gene of the present disclosure may be operably linked to an inducible, repressible, or tissue-specific promoter, as required, so as to regulate the expression level of the introduced exogenous gene at particular time or in a particular tissue, and cell type. In an embodiment, the promoter is an inducible promoter, i.e., a promoter that initiates transcription only in the presence of specific environmental conditions, developmental conditions, or inducers. Such environmental conditions include, for example, tumor acidic microenvironments, tumor hypoxic microenvironments, etc. Such inducers include, for example, doxycycline, tetracycline, or analogues thereof, wherein the analogues of tetracycline include, for example, chlortetracycline, oxytetracycline, demethylchlortetracycline, methacycline, doxycycline, and minocycline. Inducible promoters include, for example, Lac operon sequence, tetracycline operon sequence, galactose operon sequence, or doxycycline operon sequence. In another embodiment, the promoter is a repressible promoter, i.e., the expression of the exogenous gene in the cell is inhibited or the exogenous gene is not expressed in the presence of a repressor specific for the repressible promoter. Repressible promoter includes, for example, Lac repressible elements or tetracycline repressible elements. Inducible/repressible expression systems well known to those skilled in the art can be used in the present disclosure, including, but not limited to, Tet-on system, Tet-off system, Cre/loxP system, etc.

In an embodiment, the interleukin, Flt3L, XCL2, and/or XCL1 may be operably linked to a localization domain, wherein the localization domain can locate the exogenous gene of the present disclosure at a specific cellular position for expression, for example, a cell membrane, a specific organelle in the cytoplasm, e.g., endoplasmic reticulum, golgi apparatus, nucleus, etc. The localization domain includes, but is not limited to, a nuclear localization signal, a leader peptide, a transmembrane domain, and the like. In an embodiment, the exogenous genes, i.e., interleukin, Flt3L, XCL2, and/or XCL1 of the present disclosure are operably linked to the transmembrane domain, so as to be anchored on the surface of the engineered immune cell to be expressed.

In an embodiment, the exogenous gene of the present disclosure, e.g., interleukin, Flt3L, XCL2, or XCL1 protein, may be wildtype or a fusion protein or a mutant with specific properties (e.g., resistant to protease hydrolysis).

Nucleic Acid

The present disclosure further provides a nucleic acid, which contains (i) a nucleic acid sequence encoding a cell surface molecule that specifically recognizes a ligand, (ii) a nucleic acid sequence encoding an interleukin, and (iii) a nucleic acid sequence encoding Flt3L, XCL2, and/or XCL1.

In an embodiment, the cell surface molecule that specifically recognizes a ligand is a T cell receptor or a chimeric antigen receptor, preferably a chimeric antigen receptor. Definition of the chimeric antigen receptor is as described in the above.

As used herein, the term "nucleic acid molecule" includes a sequence of ribonucleotide and deoxyribonucleotide, such as modified or unmodified RNA or DNA, each in single-stranded and/or double-stranded form, linear or circular, or their mixtures (including hybrid molecules). Thus, the nucleic acid according to the present disclosure includes DNA (e.g. dsDNA, ssDNA, cDNA), RNA (e.g. dsRNA, ssRNA, mRNA, ivtRNA), their combinations or derivatives (e.g. PNA). Preferably, the nucleic acid is DNA or RNA, more preferably mRNA.

The nucleic acid may contain a conventional phosphodiester bond or an unconventional bond (e.g., amide bond, such as found in peptide nucleic acid (PNA)). The nucleic acid of the present disclosure further may contain one or more modified bases, such as, for example, trityl base and uncommon base (such as inosine). Other modifications also can be contemplated, including chemical, enzymatic, or metabolic modifications, so long as the multi-chain CAR of the present disclosure can be expressed from polynucleotides. The nucleic acid can be provided in isolated form. In an embodiment, the nucleic acid also may include a regulatory sequence, such as a transcriptional control element (including a promoter, an enhancer, an operon, a repressor, and a transcription termination signal), ribosome binding sites, and introns.

The nucleic acid sequences of the present disclosure can be codon-optimized for optimal expression in a desired host cell (e.g., immune cell); or for expression in a bacterial, yeast, or insect cell. Codon optimization refers to substitution of a codon in the target sequence that is generally rare in highly expressed genes of a given species with a codon that is generally common in highly expressed genes of such species, and the codons before and after the substitution encode the same amino acid. Therefore, the selection of an optimal codon depends on the codon usage preference of the host genome.

Vector

The present disclosure further provides a vector, containing the nucleic acid of the present disclosure. In the above, a nucleic acid sequence encoding a cell surface molecule that specifically recognizes a ligand, a nucleic acid sequence encoding IL-7, and a nucleic acid encoding XCL1, a nucleic acid encoding XCL2, and/or a nucleic acid encoding Flt3L can be located in one or more vectors.

As used herein, the term "vector" is an intermediary nucleic acid molecule used to transfer (exogenous) genetic material into a host cell, and in the host cell the nucleic acid molecule can be, for example, replicated and/or expressed. The vector generally includes targeting vectors and expression vectors. The "targeting vector" is a medium that delivers an isolated nucleic acid to the interior of a cell by, for example, homologous recombination or by using a hybrid recombinase of a sequence at specific target site. The "expression vector" is a vector used for transcription of heterologous nucleic acid sequences (for example, those sequences encoding the chimeric antigen receptor polypeptides of the present disclosure) in suitable host cells and the translation of their mRNAs. Suitable vectors that can be used in the present disclosure are known in the art, and many are commercially available. In an embodiment, the vector of the present disclosure includes, but is not limited to, plasmid, virus (e.g., retrovirus, lentivirus, adenovirus, vaccinia virus, Rous sarcoma virus (RSV), polyoma virus, and adeno-associated virus (AAV), etc.), bacteriophage, phagemid, cosmid, and artificial chromosome (including BAC and YAC). The vector itself is usually a nucleotide sequence, and usually is a DNA sequence containing an insert (transgene) and a larger sequence as "backbone" of the vector. Engineered vector typically also contains an origin autonomously replicating in the host cell (if stable expression of polynucleotide is desired), a selectable marker, and a restriction enzyme cleavage site (e.g., a multiple cloning site, MCS). The vectors may additionally contain elements such as a promoter, a poly-A tail (polyA), 3' UTR, an enhancer, a terminator, an insulator, an operon, a selectable marker, a reporter gene, a targeting sequence, and/or a protein purification tag. In a specific embodiment, the vector is an in vitro transcription vector.

Engineered Immune Cell and Preparation Method Thereof

The present disclosure further provides an engineered immune cell, which contains the nucleic acid or the vector of the present disclosure. In other words, the engineered immune cell of the present disclosure expresses a cell surface molecule that specifically recognizes a ligand, an exogenous IL-7 gene, and an XCL1, XCL2, and/or Flt3L gene.

As used herein, the term "immune cell" refers to any cell of the immune system that has one or more effector functions (e.g., cytotoxic cell killing activity, secretion of cytokines, induction of ADCC and/or CDC). For example, the immune cell may be a T cell, a macrophage, a dendritic cell, a monocyte, an NK cell, and/or an NKT cell, or an immune cell obtained from a stem cell source such as cell umbilical cord blood. Preferably, the immune cell is a T cell. The T cell may be any T cell, such as in vitro cultured T cell, for example, primary T cell, or T cell from in vitro cultured T cell line, e.g., Jurkat, SupT1, etc., or T cell obtained from a subject. Examples of subject include humans, dogs, cats, mice, rats, and transgenic species thereof. The T cell can be obtained from a variety of sources, including peripheral blood monocytes, bone marrow, lymph node tissue, umbilical blood, thymus tissue, tissue from sites of infection, ascites, pleural effusion, spleen tissue, and tumors. The T cell also may be concentrated or purified. The T cell may be at any stage of development including, but not limited to, a CD4+/CD8+ T cell, a CD4+ helper T cell (e.g., Th1 and Th2 cells), CD8+ T cell (e.g., cytotoxic T cell), tumor infiltrating cell, memory T cell, naive T cell, γδ-T cell, αβ-T cell, etc. In a preferred embodiment, the immune cell is a human T cell. The T cell can be isolated from the blood of a subject using a variety of techniques known to those of skill in the art, such as Ficoll. In the present disclosure, the immune cell is engineered to express the chimeric antigen receptor and the exogenous IL-7 gene, and the XCL1, XCL2, and/or Flt3L gene.

The nucleic acid sequence encoding the chimeric antigen receptor polypeptide and the IL-7 gene and XCL1, XCL2, and/or Flt3L gene can be introduced into an immune cell using conventional methods known in the art (e.g., by transduction, transfection, transformation). "Transfection" is a process of introducing a nucleic acid molecule or polynucleotide (including a vector) into a target cell. An example is RNA transfection, i.e., the process of introducing RNA (such as in vitro transcribed RNA, ivtRNA) into a host cell. This term is mainly used for a non-viral method in eukaryotic cells. The term "transduction" is generally used to describe virus-mediated transfer of nucleic acid molecules or polynucleotides. Transfection of animal cells typically involves opening transient pores or "holes" in the cell membrane, so as to allow uptake of material. Transfection may be carried out using calcium phosphate, by electroporation, by extrusion of cells, or by mixing cationic lipids with the material so as to produce liposomes which fuse with the cell membrane and deposit their cargo into the interior. Exemplary techniques for transfecting eukaryotic host cells include lipid vesicle-mediated uptake, heat shock-mediated uptake, calcium phosphate-mediated transfection (calcium phosphate/DNA co-precipitation), microinjection, and electroporation. The term "transformation" is used to describe the non-virus transfer of a nucleic acid molecule or polynucleotide (including a vector) to bacteria, and also to non-animal eukaryotic cells (including plant cells). Thus, the transformation is a genetic alteration of bacterial or non-animal eukaryotic cells, which is produced by direct uptake of a cell membrane from its surroundings and subsequent incorporation of exogenous genetic material (nucleic acid molecule). The transformation can be achieved by artificial means. In order for transformation to occur, the cell or bacterium must be in a competent state. For prokaryotic transformation, the techniques may include heat shock-mediated uptake, fusion to bacterial protoplasts of intact cells, microinjection, and electroporation.

Therefore, the present disclosure further provides a method of preparing an engineered immune cell, including introducing the following into the immune cell: (a) a first nucleic acid sequence encoding a cell surface molecule that specifically recognizes a ligand or the cell surface molecule that specifically recognizes a ligand encoded thereby; (b) a second nucleic acid sequence encoding IL-7 or IL-7 protein encoded thereby; and (c) a third nucleic acid sequence encoding XCL1, XCL2, and/or Flt3L or XCL1, XCL2, and/or Flt3L protein encoded thereby.

In an embodiment, the above components (a), (b), and (c) can be introduced in sequence into the immune cell in any order. In another embodiment, the above components (a), (b), and (c) can be simultaneously introduced into the immune cell, e.g., cloning (a), (b), and (c) in one or more vectors.

After introducing the nucleic acid or vector into the immune cell, a person skilled in the art could amplify and activate the resulting immune cell by conventional techniques.

Still in an embodiment, the immune cell of the present disclosure further contains at least one inactive gene selected from the group consisting of CD52, GR, TCR α, TCR β, CD3 γ, CD3 δ, CD3 ε, CD247 ζ, HLA-I, HLA-II, B2M, and immune checkpoint gene such as PD1, CTLA-4, LAG3, and TIM3. More particularly, at least TCR components (including TCR α, TCR β gene) or CD3 components (including Cd3 γ, CD3 δ, CD3 ε, CD247 ζ) in immune cells are inactivated. Such inactivation renders the TCR-CD3 complex non-functional in cells. This strategy is particularly useful for avoiding graft-versus-host disease (GvHD). Methods for inactivating a gene are known in the art, for example, by mediating DNA breakage by a meganuclease, a zincfinger nuclease, a TALE nuclease, or a Cas enzyme in a CRISPR system, thereby inactivating the gene.

Kit and Pharmaceutical Composition

The present disclosure provides a kit, which contains the engineered immune cell, the nucleic acid molecule, or the vector of the present disclosure.

In a preferred embodiment, the kit of the present disclosure further contains instructions.

The present disclosure further provides a pharmaceutical composition, which contains the engineered immune cell, the nucleic acid molecule, or the vector of the present disclosure as an active agent, and one or more pharmaceutically acceptable excipients. Therefore, the present disclosure further encompasses use of the nucleic acid molecule, the vector or the engineered immune cell in the preparation of a pharmaceutical composition or medicine.

As used herein, the term "pharmaceutically acceptable excipient" refers to a vector and/or excipient that is pharmacologically and/or physiologically compatible (i.e., capable of triggering a desired therapeutic effect without causing any undesired local or systemic effects) with the subject and active ingredient, and it is well known in the art (see, e.g., Remington's Pharmaceutical Sciences. Edited by Gennaro A R, 19th ed. Pennsylvania: Mack Publishing Company, 1995). Examples of pharmaceutically acceptable excipient include, but are not limited to, filler, binder, disintegrant, coating agent, adsorbent, anti-adherent, glidant, antioxidant, flavoring agent, colorant, sweetener, solvent, co-solvent, buffer agent, chelating agent, surfactant, diluent, wetting agent, preservative, emulsifier, cladding agent, isotonic agent, absorption delaying agent, stabilizer, and tension regulator. It is known to those skilled in the art to select a suitable excipient to prepare the desired pharmaceutical composition of the present disclosure. Exemplary excipients for use in the pharmaceutical composition of the present disclosure include saline, buffered saline, dextrose, and water. Generally, the selection of a suitable excipient depends, in particular, on the active agent used, the disease to be treated, and the desired dosage form of the pharmaceutical composition.

The pharmaceutical composition according to the present disclosure is suitable for multiple routes of administration. Generally, the application is parenterally accomplished. Parenteral delivery methods include topical, intraarterial, intramuscular, subcutaneous, intramedullary, intrathecal, intraventricular, intravenous, intraperitoneal, intrauterine, intravaginal, sublingual, or intranasal administration.

The pharmaceutical composition according to the present disclosure also can be prepared in various forms, such as solid, liquid, gaseous or lyophilized forms, particularly the pharmaceutical composition can be prepared in the form of ointment, cream, transdermal patch, gel, powder, tablet, solution, aerosol, granule, pill, suspension, emulsion, capsule, syrup, elixir, extract, tincture or liquid extract, or in a form particularly suitable for the desired method of administration. Processes known in the present disclosure for producing a medicine may include, for example, conventional mixing, dissolving, granulating, dragee-making, grinding, emulsifying, encapsulating, embedding or lyophilizing process. The pharmaceutical composition containing, for example, the immune cell as described herein is generally provided in a form of solution, and preferably contains a pharmaceutically acceptable buffer agent.

The pharmaceutical composition according to the present disclosure further may be administered in combination with one or more other agents suitable for the treatment and/or prophylaxis of diseases to be treated. Preferred examples of agent suitable for the combination include known anti-cancer medicines such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E, vincristine and doxorubicin; peptide cytotoxins, such as ricin, diphtheria toxin, pseudomonas exotoxin A, DNase and RNase; radionuclides such as iodine 131, rhenium 186, indium 111, iridium 90, bismuth 210 and 213, actinides 225 and astatine 213; prodrugs such as antibody-directed enzyme prodrugs; immunostimulatory agents such as platelet factor 4, and melanoma growth stimulating protein; antibodies or fragments thereof, such as anti-CD3 antibodies or fragments thereof, complement activators, heterologous protein domains, homologous protein domains, viral/bacterial protein domains and viral/bacterial peptides. In addition, the pharmaceutical composition of the present disclosure also can be used in combination with one or more other treatment methods, such as chemotherapy and radiotherapy.

Therapeutic Use

The present disclosure further provides a method of treating a subject with cancer, infection or autoimmune disease, including administering to the subject an effective amount of the immune cell or the pharmaceutical composition according to the present disclosure. Therefore, the present disclosure also encompasses use of the engineered immune cell in the preparation of a medicine for treating cancer, infection, or autoimmune diseases.

In an embodiment, an effective amount of the immune cell and/or the pharmaceutical composition of the present disclosure is directly administered to the subject.

In another embodiment, the treatment method of the present disclosure is ex vivo treatment. Specifically, the method includes the steps of: (a) providing a sample, the sample containing an immune cell; (b) introducing the chimeric antigen receptor of the present disclosure and an exogenous gene to be expressed into the immune cell in vitro to obtain a modified immune cell, and (c) administering the modified immune cell to the subject in need thereof. Preferably, the immune cell provided in step (a) is selected from a macrophage, a dendritic cell, a monocyte, a T cell, an NK cell, and/or an NKT cell; and the immune cell can be obtained from the sample (particularly a blood sample) of the subject by conventional methods known in the art. However, other immune cells capable of expressing the chimeric antigen receptor and exogenous gene of the present disclosure and exerting the desired biological effect function as described herein also can be used. Besides, the immune cells generally selected are compatible with the subject's immune system, i.e., it is preferred that the immune cells do not trigger an immunogenic response. For example, a "universal recipient cell", i.e., a universally compatible lymphocyte exerting a desired biological effect function and being capable of growing and amplifying in vitro, can be used. The use of such cells will not require obtaining and/or providing the subject's own lymphocyte. The ex vivo introduction of step (c) may be carried out by introducing the nucleic acid or vector described herein into the immune cell via electroporation or by infecting the immune cell with a viral vector, wherein the viral vector is a lentiviral vector, adenoviral vector, adeno-associated viral vector or retroviral vector as previously described. Other conceivable methods include using a transfection reagent (such as a liposome) or transient RNA transfection.

In an embodiment, the immune cell is an autologous or allogeneic cell, preferably T cell, macrophage, dendritic cell, monocyte, NK cell and/or NKT cell, more preferably T cell, NK cell or NKT cell.

As used herein, the term "autologous" means that any material derived from an individual will be later re-introduced into the same individual.

As used herein, the term "allogeneic" means that the material is derived from a different animal or different patient of the same species as the individual into which the material is introduced. When the genes at one or more loci are different, two or more individuals are considered allogeneic to each other. In some cases, genetic differences in allogeneic material from various individuals of the same species may be sufficient for antigen interactions to occur.

As used herein, the term "subject" refers to a mammal. The mammal may be, but is not limited to, a human, a non-human primate, a mouse, a rat, a dog, a cat, a horse, or a cow. Mammals other than human can be advantageously used as subjects representing cancer animal models. Preferably, the subject is a human.

In an embodiment, the cancer is a cancer associated with expression of the target to which the ligand binding domain binds. For example, the cancer includes, but is not limited to, brain glioma, blastoma, sarcoma, leukemia, basal cell carcinoma, biliary tract cancer, bladder cancer, bone cancer, brain and CNS cancer, breast cancer, peritoneal cancer, cervical cancer, choriocarcinoma, colon and rectal cancer, connective tissue cancer, cancer of digestive system, endometrial cancer, esophageal cancer, eye cancer, head and neck cancer, stomach cancer (including gastrointestinal cancer), glioblastoma (GBM), liver cancer, hepatoma, intraepithelial tumor, kidney cancer, larynx cancer, liver tumor, lung cancer (such as small cell lung cancer, non-small cell lung cancer, lung adenocarcinoma and squamous lung cancer), lymphoma (including Hodgkin's lymphoma and non-Hodgkin's lymphoma), melanoma, myeloma, neuroblastoma, oral cancer (e.g., lips, tongue, mouth, and pharynx), ovarian cancer, pancreatic cancer, prostate cancer, retinoblastoma, rhabdomyosarcoma, rectal cancer, cancer of respiratory system, salivary gland cancer, skin cancer, squamous cell carcinoma, stomach cancer, testicular cancer, thyroid cancer, uterine or endometrial cancer, malignant tumor of urinary system, vulval cancer and other cancers and sarcomas, and B cell lymphoma (including low-grade/follicular non-Hodgkin's lymphoma (NHL), small lymphocytic (SL) NHL, intermediate-grade/follicular NHL, intermediate-grade diffuse NHL, high-grade immunoblastic NHL, high-grade lymphoblastic NHL, high-grade small non-cracked cell NHL, bulky disease NHL), mantle cell lymphoma, AIDS-related lymphoma, and Waldenstrom macroglobulinemia, chronic lymphocytic leukemia (CLL), acute lymphocytic leukemia (ALL), B cell acute lymphocytic leukemia (B-ALL), T cell acute lymphocytic leukemia (T-ALL), B cell prolymphocytic leukemia, blast cell plasmacytoid dendritic cell tumor, Burkitt lymphoma, diffuse large B cell lymphoma, follicular lymphoma, chronic myelogenous leukemia (CML), malignant lymphoproliferative disorder, MALT lymphoma, hairy cell leukemia, marginal zone lymphoma, multiple myeloma, myelodysplasia, plasmablastic lymphoma, preleukemia, plasmacytoid dendritic cell tumor, post-transplant lymphoproliferative disorder (PTLD), and other diseases associated with target expression. Preferably, the disease which can be treated with the engineered immune cell or the pharmaceutical composition of the present disclosure is selected from the group consisting of: leukemia, lymphoma, multiple myeloma, brain glioma, pancreatic cancer, gastric cancer, and so on.

In an embodiment, the infection includes, but is not limited to, infections caused by viruses, bacteria, fungi, and parasites.

In an embodiment, the autoimmune disease includes, but is not limited to, type I diabetes, celiac disease, Graves disease, inflammatory bowel disease, multiple sclerosis, psoriasis, rheumatoid arthritis, Addison disease, sicca syndrome, Hashimoto thyroiditis, myasthenia gravis, vasculitis, pernicious anemia, and systemic lupus erythematosus, etc.

In an embodiment, the method further includes administering to the subject one or more additional chemotherapeutic agents, biological agents, medicines, or treatments. In this embodiment, the chemotherapeutic agents, biological agents, medicines, or treatments are selected from the group consisting of radiotherapy, surgery, antibody reagent and/or small molecule and any combination thereof.

The present disclosure will be described in detail below with reference to the accompanying drawings and examples.

It should be noted that those skilled in the art should understand that the accompanying drawings of the present disclosure and examples thereof are only for illustrative purpose, and cannot constitute any limitation to the present disclosure. The examples of the present disclosure and the features in the examples may be combined with each other without contradiction.

SPECIFIC EMBODIMENTS

Example 1 Construction of Mouse Pancreatic Cancer Cell Line Panc02-mCD19

1. Preparation of pLV-mCD19 Plasmid

With mouse spleen total mRNA as a template, a mouse spleen total cDNA sequence was obtained by reverse transcription PCR, and then a mouse mCD19 sequence containing XbaI and SalI restriction sites was obtained by PCR. The mCD19 gene was then recombined into a pLV-BHAm plasmid, to obtain a pLV-BHAm-mCD19 plasmid.

2. Lentivirus Packaging

In a T175 culture flask, 293T cells were inoculated in 30 ml of DMEM medium containing 10% fetal bovine serum at a density of $30\times10^6$ cells/flask, and incubated overnight in an incubator at 37° C. and 5% $CO_2$.

In a sterile tube, 3 ml of Opti-MEM (Gibco, Lot No. 31985-070), 34 μg of pLV-BHAm-mCD19 plasmid, 8.5 μg of pMD2. G vector (Addgene, Lot No. 12259), and 17 μg of psPAX2 vector (Addgene, Lot No. 12260) were added. Then, 120 μl of X-treme GENE HP DNA transfection reagent (Roche, Lot. No. 06366236001) was added, well mixed immediately, followed by incubation at room temperature for 15 min. Then the plasmid/vector/transfection reagent mixture was added dropwise into the culture flask of 293T cells prepared in advance, and cultured overnight under a condition of 5% $CO_2$ at 37° C. Cultures were collected 24 hours and 48 hours after transfection, and after combination, ultracentrifugation (25000 g, 4° C., 2.5 h) was performed to obtain a concentrated pLV-BHAm-mCD19 lentivirus, which was stored at −80° C.

3. Screening of Panc02-mCD19 Cell Line

RPMI-1640 medium (Gibco, Lot No. C12430500BT) containing 10% fetal bovine serum, $1\times10^6$ mouse pancreatic cancer cells Panc02 (donated by laboratory of China Pharmaceutical University), and 200 μl of pLV-BHAm-mCD19 lentivirus were added to each well of a 6-well cell culture plate, and incubated at 37° C. under a condition of 5% $CO_2$ for 48 h. Cells were then digested with 0.25% pancreatin into single cell suspension, and diluted and transferred to a 96-well plate for continued culture, until monoclonal cells appeared. Monoclonal cells were picked, digested again with 0.25% pancreatin into single cells, and the cells were resuspended with 200 μl of opti-MEM medium. Infection efficiency was detected by flow cytometry with APC anti-mouse CD19 antibody (Biolegend, Lot No. 115512), and CD19 positive clones were screened. After the positive clones were passaged 3-4 times, CD19 expression level was detected by flow cytometry. Panc02 cells not infected by virus were used as control.

Figure 3:
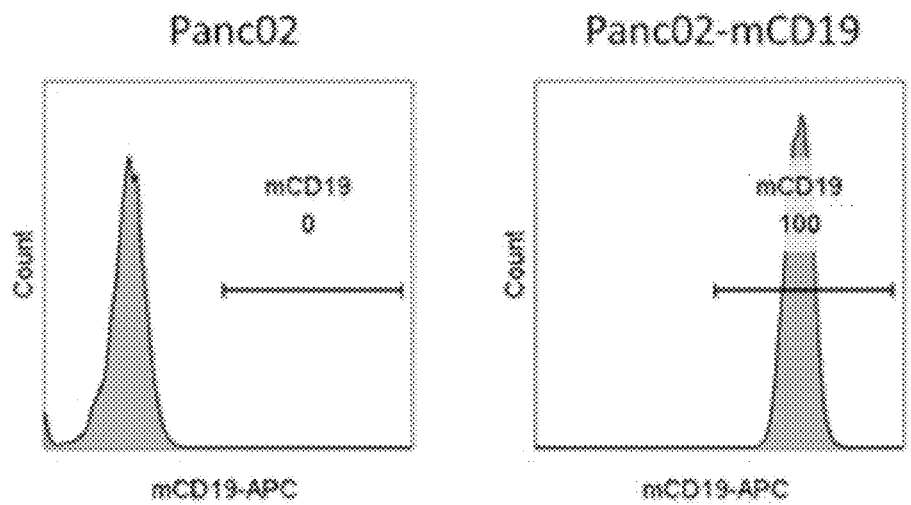
FIG. 3: CD19 expression rate of Panc02-mCD19 cells.

Results are as shown in FIG. 3. In the finally screened Panc02-mCD19 cell line, the CD19 expression rate is 100%.

Example 2. Preparation of CAR-T Cell

1. Construction of Retroviral Plasmid

Encoding sequence fragments of mCD19-scFv, mCD8a hinge region and transmembrane region, murine 41bb intracellular domain and murine CD3 intracellular domain, which were linked in sequence, were artificially synthesized, and an XhoI/EcoRI enzyme site was added at two ends. The fragment was cloned into an MSCV vector, to obtain an MSCV-mCD19-CAR plasmid.

Encoding sequence fragments of T2A and murine IL-7 successively linked were artificially synthesized, and an EcoRI/SalI enzyme site was added at two ends. The fragment was cloned into the MSCV-mCD19-CAR vector, to obtain an MSCV-mCD19-CAR-IL-7 plasmid.

Encoding sequence fragments of T2A and murine XCL1 successively linked were artificially synthesized, and an EcoRI/SalI enzyme site was added at two ends. The fragment was cloned into the MSCV-mCD19-CAR vector, to obtain an MSCV-mCD19-CAR-XCL1 plasmid.

Encoding sequence fragments of T2A and murine CCL19 successively linked were artificially synthesized, and an EcoRI/SalI enzyme site was added at two ends. The fragment was cloned into the MSCV-mCD19-CAR vector, to obtain an MSCV-mCD19-CAR-CCL19 plasmid.

Encoding sequence fragments of T2A and murine Flt3L successively linked were artificially synthesized, and an EcoRI/SalI enzyme site was added at two ends. The fragment was cloned into the MSCV-mCD19-CAR vector, to obtain an MSCV-mCD19-CAR-Flt3L plasmid.

2. Preparation of Retrovirus

In a T175 culture flask, 293T cells were inoculated in 30 ml of DMEM medium containing 10% fetal bovine serum at a density of $30 \times 10^6$ cells/flask, and incubated overnight in an incubator at 37° C. and 5% $CO_2$ for viral packaging.

In a sterile tube, 3 ml of Opti-MEM (Gibco, Lot No. 31985-070), 45 μg of retrovirus plasmid (MSCV-mCD19-CAR plasmid, MSCV-mCD19-CAR-IL-7 plasmid, MSCV-mCD19-CAR-XCL1 plasmid, MSCV-mCD19-CAR-CCL19 or MSCV-mCD19-CAR-Flt3L plasmid), and 15 μg of packaging vector pCL-Eco (Shanghai Hebio Biotechnology Co., Ltd, Lot No. P3029) were added. Then, 120 μl of X-treme GENE HP DNA transfection reagent (Roche, Lot. No. 06366236001) was added, well mixed immediately, followed by incubation at room temperature for 15 min. Then the plasmid/vector/transfection reagent mixture was added dropwise into the culture flask of 293T cells prepared in advance, and cultured overnight under a condition of 5% $CO_2$ at 37° C. Cultures were collected 72 hours after transfection, and centrifuged (2000 g, 4° C., 10 min) to obtain retrovirus supernatant.

3. Preparation of CAR-T Cell

T lymphocytes were isolated from mouse spleens, and the T cells were activated with DynaBeads CD3/CD28 CTS™ (Gibco, Lot. No. 40203D), and cultured in 5% $CO_2$ at 37° C. for 1 day.

The activated T cells were inoculated into a 24-well plate pre-coated with RetroNectin overnight at a density of $3 \times 10^6$ cells/mL per well, then 500 μL of complete medium (NT, control), MSCV-mCD19-CAR virus, MSCV-mCD19-CAR-XCL1 virus, MSCV-mCD19-CAR-Flt3L virus, MSCV-mCD19-CAR-IL-7 virus+MSCV-mCD19-CAR-CCL19 virus, MSCV-mCD19-CAR-IL-7 virus+MSCV-mCD19-CAR-Flt3L virus, or MSCV-mCD19-CAR-IL-7 virus+MSCV-mCD19-CAR-XCL1 virus was added, respectively, and the complete medium was supplemented to 2 mL.

The 24-well plate was placed in a centrifuge for centrifuging infection, and centrifuged at 2000 g at 32° C. for 2 h. Then, the 24-well plate was immediately placed in a $CO_2$ incubator at 37° C. for static culture. The medium was replaced with fresh medium the next day, and the cell density was adjusted to $1 \times 10^6$ cells/mL. Three days after infection, the cells were collected for subsequent analysis. The collected cells were NT cells, mCD19-CAR cells, mCD19-CAR-XCL1 cells, mCD19-CAR-Flt3L cells, mCD19-CAR-IL-7-CCL19 cells, mCD19-CAR-IL-7-Flt3L cells, and mCD19-CAR-IL-7-XCL1 cells.

Example 3. Detection of Expression of CAR-T Cell

Figure 4:
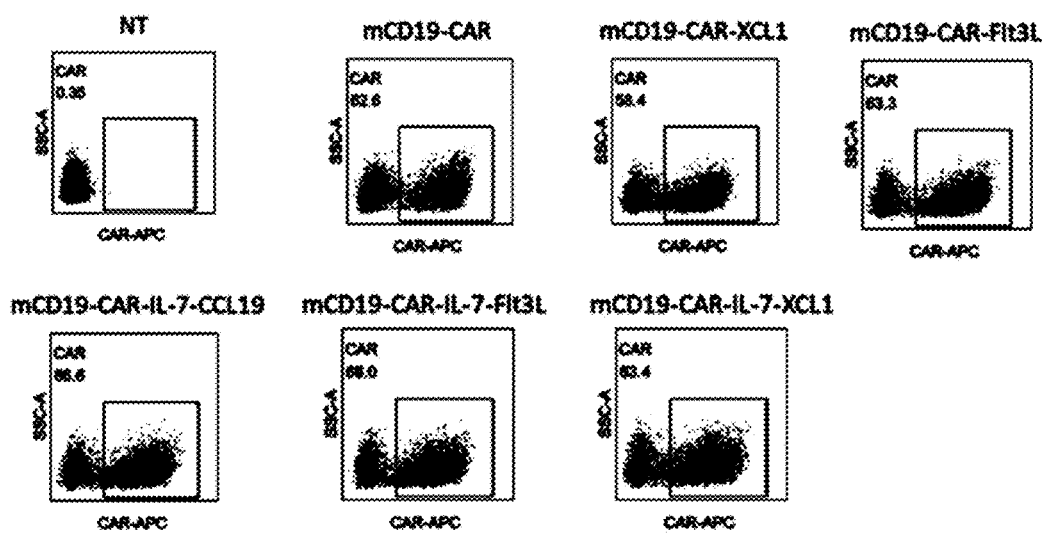
FIG. 4: CAR expression levels of CAR-T cells detected by flow cytometry.

1. Expression Level of CAR on Cell Surface $2 \times 10^5$ CAR-T cells prepared in Example 2 were taken out, and the expression level of CAR on CAR T cells was detected by flow cytometry with Goat Anti-Rat IgG (H&L) Biotin (BioVision, Lot No. 6910-250) as a primary antibody, and APC Streptavidin (BD Pharmingen, Lot No. 554067) as a secondary antibody. Results are as shown in FIG. 4.

It can be seen that compared with the control, the CAR positive efficiency in mCD19-CAR, mCD19-CAR-XCL1, mCD19-CAR-Flt3L, mCD19-CAR-IL-7-XCL1, mCD19-CAR-IL-7-CCL19 cells and mCD19-CAR-IL-7-Flt3L cells is greater than 50%, indicating that all these cells can effectively express CAR.

2. Expression Level of XCL1

Figure 5:
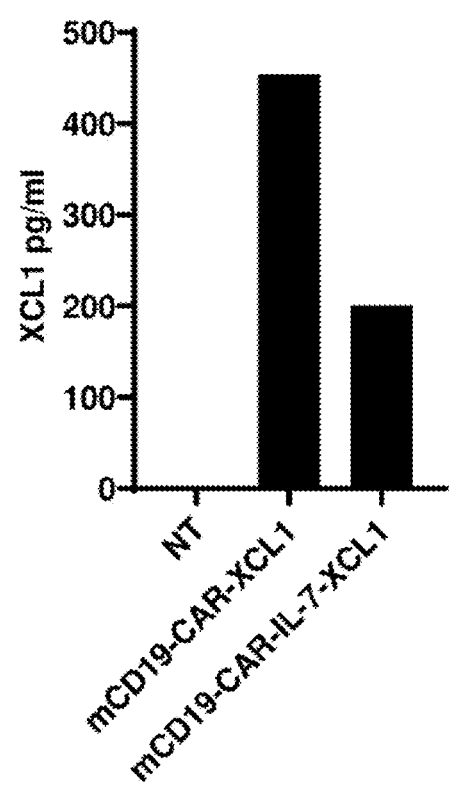
FIG. 5: XCL1 expression levels of CAR-T cells detected by ELISA.

The supernatant of the CAR-T cells prepared in Example 2 was collected, and the XCL1 secretion level in the cells was detected with a Mouse XCL1 DuoSet ELISA kit (R&D Systems, Lot No. DY486) according to the manufacturer's recommendations. Results are as shown in FIG. 5.

It can be seen that two CAR T cells containing mCD19-CAR-XCL1 both can effectively secrete XCL1.

3. Expression Level of IL-7

Figure 6:
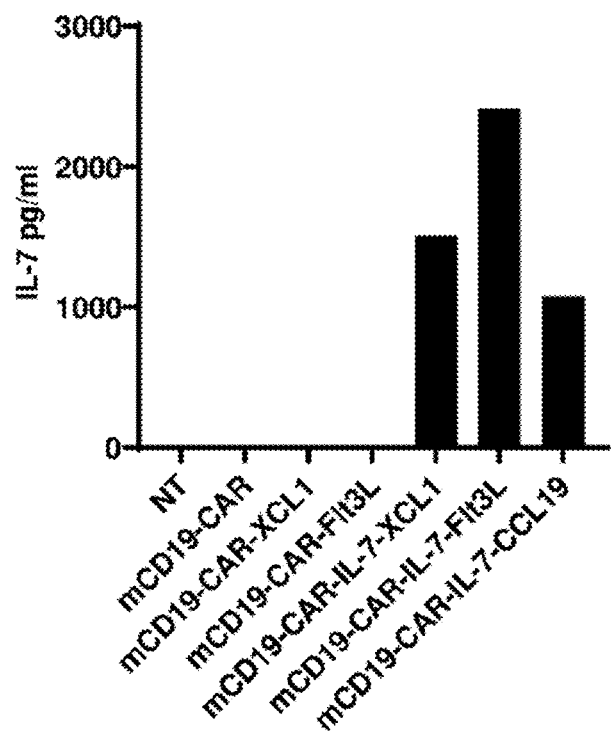
FIG. 6: IL-7 expression levels of CAR-T cells detected by ELISA.

The supernatant of the CAR-T cells prepared in Example 2 was collected, and the IL-7 secretion level in the cells was detected with a Mouse IL-7 DuoSet ELISA kit (R&D Systems, Lot No. DY407) according to the manufacturer's recommendations. Results are as shown in FIG. 6.

It can be seen that all of the three CART cells containing mCD19-CAR-IL-7 can effectively express IL-7.

4. Expression Level of CCL19

Figure 7:
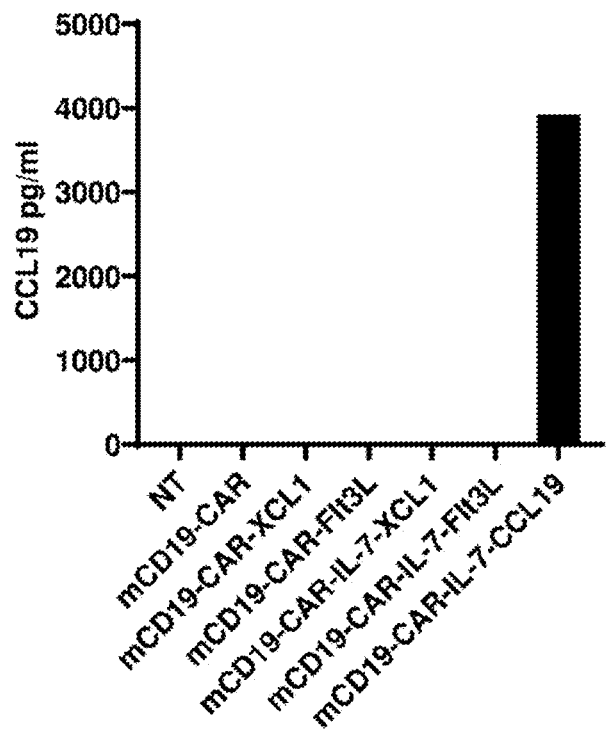
FIG. 7: CCL19 expression levels of CAR-T cells detected by ELISA.

The supernatant of the CAR-T cells prepared in Example 2 was collected, and the CCL19 secretion level in the cells was detected with a Mouse CCL19 DuoSet ELISA kit (R&D Systems, Lot No. DY440) according to the manufacturer's recommendations. Results are as shown in FIG. 7.

It can be seen that CAR T cells containing mCD19-CAR-CCL19 can effectively express CCL19.

5. Expression Level of Flt3L

Figure 8:
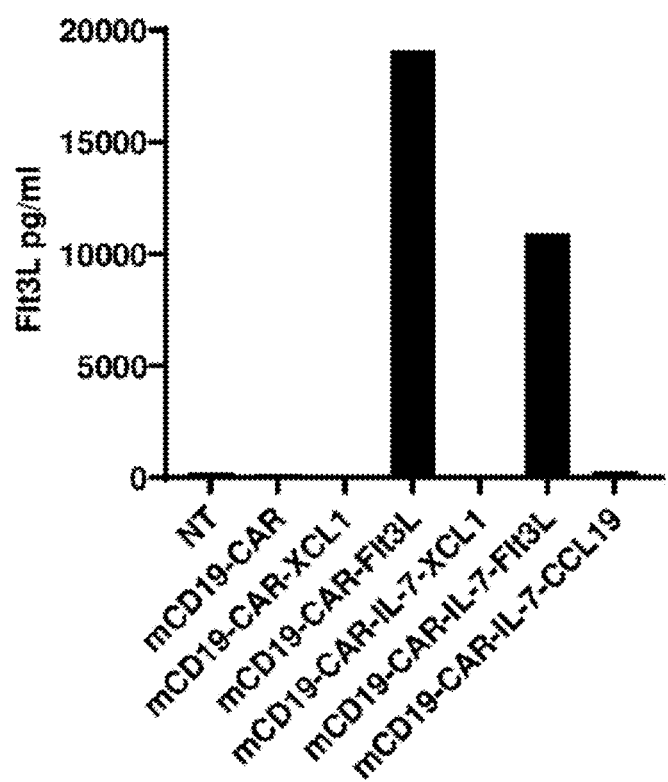
FIG. 8: Flt3L expression levels of CAR-T cells detected by ELISA.

The supernatant of the CAR-T cells prepared in Example 2 was collected, and the Flt3L secretion level in the cells was detected with a Mouse Flt-3 Ligand DuoSet ELISA kit (R&D Systems, Lot No. DY427) according to the manufacturer's recommendations. Results are as shown in FIG. 8.

It can be seen that the two CAR T cells containing mCD19-CAR-Flt3L both can effectively express Flt3L.

Example 4. Detection of IFN-γ Secretion Level of CAR-T Cell

The NT cells, mCD19-CAR cells, mCD19-CAR-XCL1 cells, mCD19-CAR-Flt3L cells, mCD19-CAR-IL-7-CCL19 cells, mCD19-CAR-IL-7-Flt3L cells, and mCD19-CAR-IL-7-XCL1 cells were added to a 96-well round bottom plate at a concentration of $2 \times 10^5$ cells/100 μl, respectively. Target Panc02-mCD19 cells or non-target Panc02 cells were then added to each well at a concentration of $1 \times 10^4$ cells/100 μl, respectively. Culture supernatant was collected after 24 h of culture at 37° C. The expression level of IFN-γ in culture supernatant was detected with a Mouse IFN-gamma DuoSet ELISA kit (R&D, Lot No. DY485) according to the manufacturer's recommendations.

Figure 9:
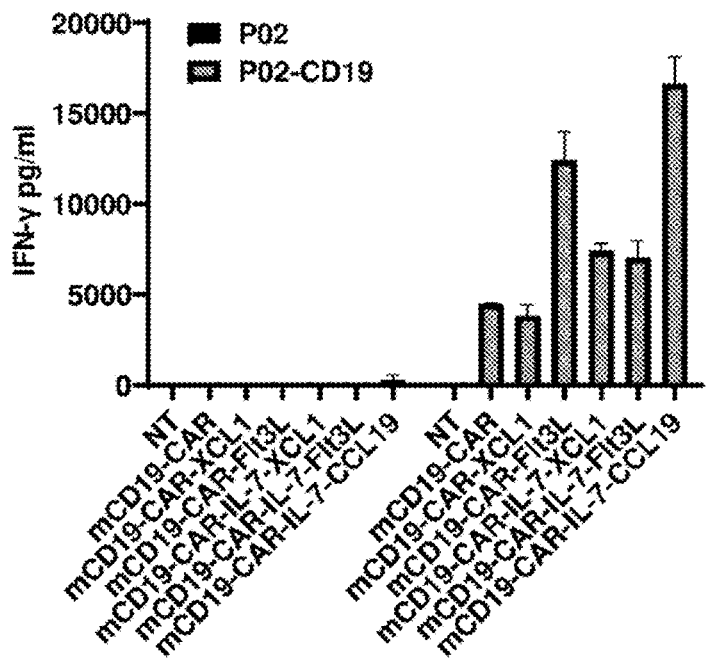
FIG. 9: IFN-γ release levels after co-culture of CAR-T cells with target cells and non-target cells, respectively.

The detection result is as shown in FIG. 9. It can be seen that no release of IFN-γ is detected in the non-target cell Panc02, and the NT cell does not express IFN-γ, indicating that killing of the CAR T cell in the present example is specific. Moreover, when killing target cells, compared with T cell expressing only CAR, additionally expressing Flt3L, IL-7+Flt3L, IL-7+CCL19 or IL-7+XCL1 can significantly increase the antigen-specific IFN-γ level.

Example 5. Verification of Tumor Inhibition Effect of CAR-T Cell $5 \times 10^5$ Panc02-mCD19 pancreatic cancer cells prepared in Example 1 were subcutaneously inoculated in left-forelimb axilla region of healthy C57BL/6 mice.

The mice inoculated with pancreatic cancer cells were randomly divided into 7 groups, with 6 mice in each group. When the tumor volume reaches 100 mm³, each mouse was injected with $5 \times 10^6$ NT cells, mCD19-CAR cells, mCD19-CAR-XCL1 cells, mCD19-CAR-Flt3L cells, mCD19-CAR-IL-7-CCL19 cells, mCD19-CAR-IL-7-Flt3L cells, or mCD19-CAR-IL-7-XCL1 cells prepared in Example 2 through tail vein.

Changes of body weight and tumor volume of the mice were monitored until the end of the experiment.

Figure 10:
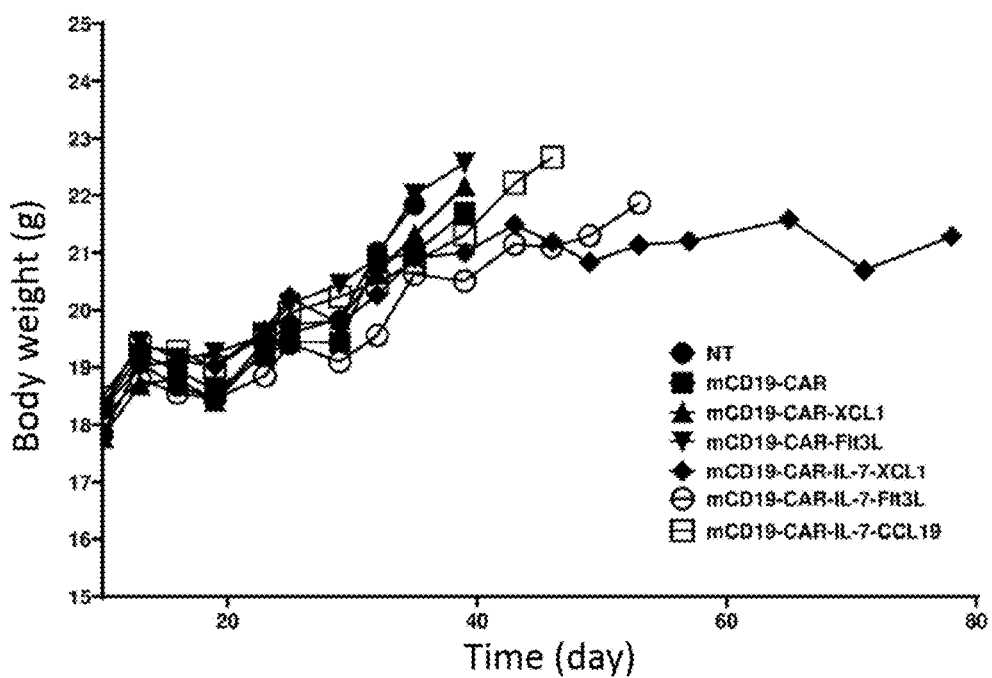
FIG. 10: Curves of body weight change of mice after treating pancreatic cancer in mice with CAR-T cells.

The changes of body weight of the mice are shown in FIG. 10. It can be seen that after the administration of CAR-T cells, the body weight of each group of mice is not significantly different compared with that of the control group, and in the observation period, when the tumor of the mice does not exceed 1500 mm³, the mice are active and have a normal hair color, which indicates that the administration of CAR-T cells will not have obvious toxic side effects on the mice.

Figure 11:
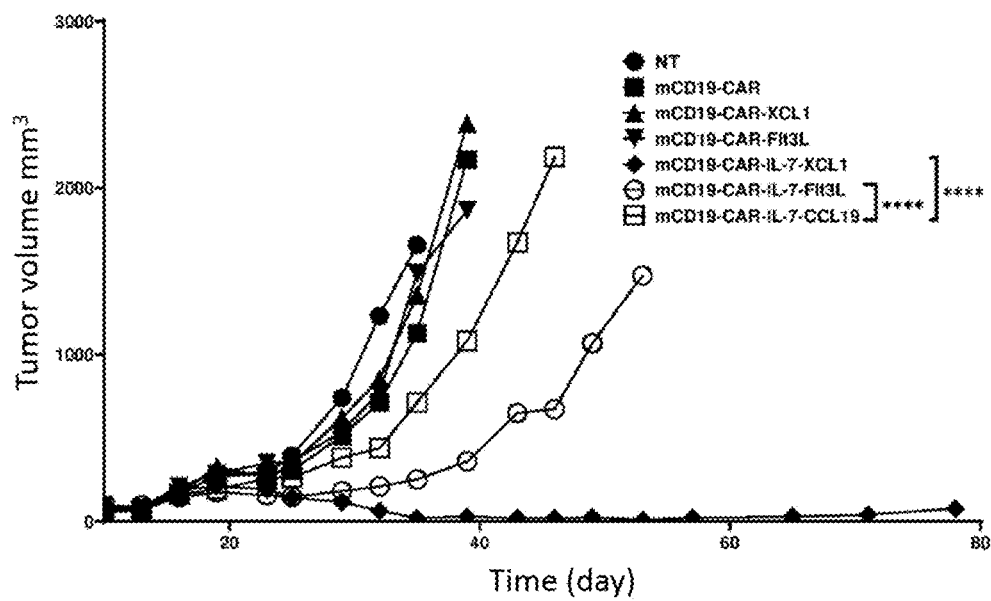
FIG. 11: Curves of tumor growth of mice after treating pancreatic cancer in mice with CAR-T cells.

The changes of tumor volume of the mice are shown in FIG. 11. It can be seen that compared with the NT cells and the conventional CAR-T cells, the CAR-T cells expressing only XCL1 or Flt3L cannot significantly enhance the anti-tumor effect, indicating that the XCL1 or Flt3L alone cannot exhibit a synergistic effect with the CAR-T cells. Besides, the anti-tumor effect of CAR-T cells co-expressing IL-7 and CCL19 was obviously superior to that of conventional CAR-T cells, which is consistent with previous reports. However, unexpectedly, the inventors found that the combinations of IL-7+XCL1 and IL-7+Flt3L not only significantly increase the tumor inhibition effect of CAR-T cells, but also the enhancement effect is far superior to that of the IL-7+CCL19 combination for CAR-T. In the above, CAR-T cells co-expressing IL-7 and XCL1 have the best tumor inhibition effect, and almost completely eliminate the tumor without significant recurrence.

Figure 12:
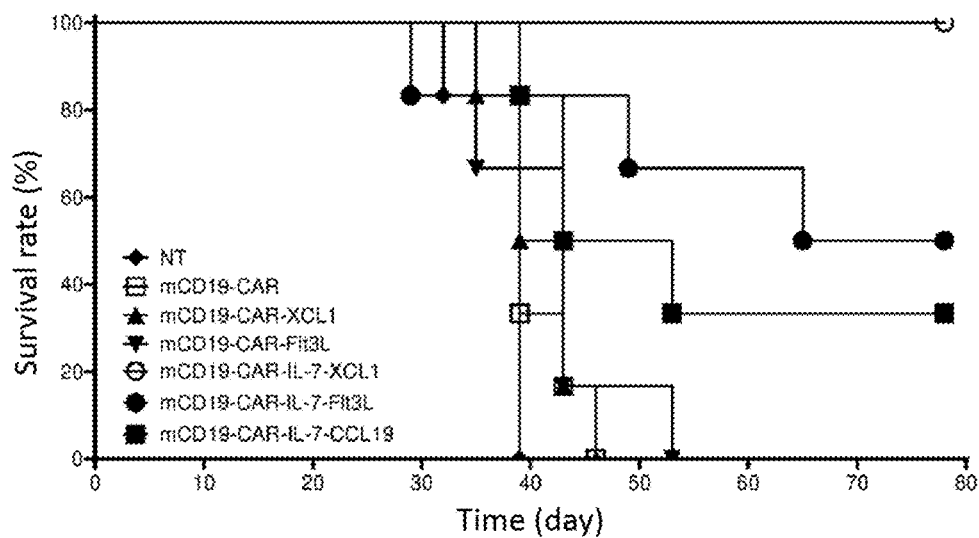
FIG. 12: Survival curves of mice after treating pancreatic cancer in mice with CAR-T cells.

The survival curves of the mice are shown in FIG. 12. It can be seen that compared with conventional CAR-T cell therapy, the additionally expressed XCL1 or Flt3L alone cannot significantly prolong the survival time of the mice, and CAR-T cells co-expressing IL-7+CCL19, IL-7+Flt3L or IL-7+XCL1 can effectively prolong the survival time of the mice. In the above, in the IL-7+XCL1 group, five mice were in complete remission, and remained tumor-free survival until the end of the experiment, and one mouse achieved a quite good partial remission and continuously maintained a tumor suppression state. In the IL-7+Flt3L group, three mice maintained complete remission at the end of the experiment. But in the IL-7+CCL19 group, two mice maintained complete remission at the end of the experiment, and remained tumor-free survival. For the remaining mice, although a certain tumor inhibition effect was exerted compared with conventional CAR-T cells at the early stage of the experiment, the tumor inhibition effect disappeared at a later stage of the experiment, causing death of the mice.

The above results show that co-expression of IL-7+XCL1 or IL-7+Flt3L can effectively enhance the inhibitory effect of the engineered immune cell on the target pancreatic cancer cell, significantly improve the survival rate, and the enhanced effect is superior to the currently known IL-7+CCL19 combination.

It should be noted that the above-mentioned are merely for preferred examples of the present disclosure and not used to limit the present disclosure. For one skilled in the art, various modifications and changes may be made to the present disclosure. Those skilled in the art should understand that any amendments, equivalent replacements, improvements, and so on, made within the spirit and principle of the present disclosure, should be covered within the scope of protection of the present disclosure.

What is claimed is:

1. An engineered immune cell, which expresses (i) a cell surface molecule that specifically recognizes a ligand, (ii) an exogenous IL-7, and (iii) an exogenous XCL2 and/or XCL1 gene.

2. The engineered immune cell according to claim 1, wherein the cell surface molecule that specifically recognizes a ligand is a chimeric antigen receptor or a T cell receptor.

3. The engineered immune cell according to claim 2, wherein the cell surface molecule that specifically recognizes a ligand is the chimeric antigen receptor containing a ligand binding domain, a transmembrane domain, a co-stimulatory domain, and an intracellular signaling domain.

4. The engineered immune cell according to claim 1, wherein an encoding gene of the IL-7 is represented by SEQ ID NO: 23 or 27, or the IL-7 is represented by SEQ ID NO: 24 or 28.

5. The engineered immune cell according to claim 1, wherein the XCL1 gene is represented by SEQ ID NO: 25 or 29, or a polypeptide encoded by the XCL1 gene is represented by SEQ ID NO: 26 or 30.

6. The engineered immune cell according to claim 1, wherein the XCL2 gene is represented by SEQ ID NO: 67, or a polypeptide encoded by the XCL2 gene is represented by SEQ ID NO: 68.

7. The engineered immune cell according to claim 1, wherein the immune cell is selected from the group consisting of a T cell, a macrophage, a dendritic cell, a monocyte, an NK cell and an NKT cell.

8. The engineered immune cell according to claim 7, wherein the T cell is a CD4+/CD8+ T cell, a CD4+ helper T cell, a CD8+ T cell, a tumor infiltrating cell, a memory T cell, a naive T cell, a γδ-T cell, or an αβ-T cell.

9. The engineered immune cell according to claim 3, wherein the ligand binding domain is selected from the group consisting of scFv, Fab, single domain antibody, nanobody, antigen binding ligand, recombinant fibronectin domain, anticalin and DARPIN.

10. The engineered immune cell according to claim 3, wherein the ligand binding domain binds to a target selected from the group consisting of: TSHR, CD19, CD123, CD22, BAFF-R, CD30, CD171, CS-1, CLL-1, CD33, EGFRvIII, GD2, GD3, BCMA, GPRCSD, Tn antigen, PSMA, ROR1, FLT3, FAP, TAG72, CD38, CD44v6, CEA, EPCAM, B7H3, KIT, IL-13Ra2, mesothelin, IL-1 1Ra, PSCA, PRSS21, VEGFR2, LewisY, CD24, PDGFR-β, S SEA-4, CD20, AFP, Folate receptor α, ERBB2 (Her2/neu), MUC1, EGFR, CS1, CD138, NCAM, Claudin18.2, Prostase, PAP, ELF2M, Ephrin B2, IGF-I receptor, CAIX, LMP2, gp100, bcr-ab1, tyrosinase, EphA2, Fucosyl GM1, sLe, GM3, TGS5, HMW-MAA, o-acetyl-GD2, Folate receptor β, TEM1/CD248, TEM7R, CLDN6, GPRCSD, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1 a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, TMPRSS2 ETS fusion gene, NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, NKG2D and any combination thereof.

11. The engineered immune cell according to claim 3, wherein the transmembrane domain is a transmembrane domain of a protein selected from the group consisting of: TCR α chain, TCR β chain, TCR γ chain, TCR δ chain, CD3 ζ subunit, CD3 ε subunit, CD3 γ subunit, CD3 δ subunit, CD45, CD4, CD5, CD8 a, CD9, CD16, CD22, CD33, CD28, CD37, CD64, CD80, CD86, CD134, CD137 and CD154.

12. The engineered immune cell according to claim 3, wherein the intracellular signaling domain is a signaling domain of a protein selected from the group consisting of: FcR γ, FcR β, CD3 γ, CD3 δ, CD3 ε, CD3 ζ, CD22, CD79a, CD79b, and CD66d.

13. The engineered immune cell according to claim 3, wherein the co-stimulatory domain is one or more co-stimulatory signaling domains of a protein selected from the group consisting of: TLR1, TLR2, TLR3, TLR4, TLR5, TLR6, TLR7, TLR8, TLR9, TLR10, CARD11, CD2, CD7, CD8, CD18, CD27, CD28, CD30, CD40, CD54, CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM and ZAP70.

14. The engineered immune cell according to claim 1, wherein the immune cell further contains at least one inactive gene selected from the group consisting of CD52, GR, TCR α, TCR β, CD3 γ, CD3 δ, CD3 ε, CD247 ζ, HLA-I, HLA-II, B2M, PD1, CTLA-4, LAG3 and TIM3.

15. The engineered immune cell according to claim 1, wherein expression of the IL-7, XCL2, and/or XCL1 gene is a conditional expression.

16. The engineered immune cell according to claim 15, wherein the IL-7, XCL2, and/or XCL1 gene is operably linked to an inducible, repressible, or tissue-specific promoter so as to be conditionally expressed.

17. A nucleic acid molecule, which contains: (i) a nucleic acid sequence encoding a cell surface molecule that specifically recognizes a ligand, (ii) a nucleic acid sequence encoding an IL-7, and (iii) a nucleic acid sequence encoding XCL2 and/or XCL1.

18. The nucleic acid molecule according to claim 17, wherein the cell surface molecule that specifically recognizes a ligand is a chimeric antigen receptor.

19. A vector, which contains the nucleic acid molecule according to claim 17.

20. The vector according to claim 19, wherein the vector is selected from the group consisting of plasmid, retrovirus, lentivirus, adenovirus, vaccinia virus, Rous Sarcoma Virus (RSV), polyoma virus, and adeno-associated virus (AAV).

21. A pharmaceutical composition, which contains the engineered immune cell according to claim 1.

22. The pharmaceutical composition according to claim 21, wherein said composition is for treating cancers, infections or autoimmune diseases.

* * * * *

SEQUENCE LISTING

<160> NUMBER OF SEQ ID NOS: 68

<210> SEQ ID NO 1
<211> LENGTH: 726
<212> TYPE: DNA
<213> ORGANISM: Artificial Sequence
<220> FEATURE:
<223> OTHER INFORMATION: CD19 scFv

<400> SEQUENCE: 1

```
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggagatcac aggtggcggt ggctcgggcg gtggtgggtc gggtggcggc     360
```

```
ggatctgagg tgaaactgca ggagtcagga cctggcctgg tggcgccctc acagagcctg      420
tccgtcacat gcactgtctc aggggtctca ttacccgact atggtgtaag ctggattcgc      480
cagcctccac gaaagggtct ggagtggctg ggagtaatat ggggtagtga aaccacatac      540
tataattcag ctctcaaatc cagactgacc atcatcaagg acaactccaa gagccaagtt      600
ttcttaaaaa tgaacagtct gcaaactgat gacacagcca tttactactg tgccaaacat      660
tattactacg gtggtagcta tgctatggac tactggggcc aaggaacctc agtcaccgtc      720
tcctca                                                                 726
```

```
<210> SEQ ID NO 2
<211> LENGTH: 242
<212> TYPE: PRT
<213> ORGANISM: Artificial Sequence
<220> FEATURE:
<223> OTHER INFORMATION: CD19 scFv

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 3
<211> LENGTH: 75
<212> TYPE: DNA
<213> ORGANISM: Artificial Sequence
<220> FEATURE:
<223> OTHER INFORMATION: CD8alpha transmembrane domain
```

<400> SEQUENCE: 3

```
atctacatct gggcgcccct tggccgggact tgtggggtcc ttctcctgtc actggttatc    60 acccttact gcaaa                                                      75
```

<210> SEQ ID NO 4
<211> LENGTH: 25
<212> TYPE: PRT
<213> ORGANISM: Artificial Sequence
<220> FEATURE:
<223> OTHER INFORMATION: CD8alpha transmembrane domain

<400> SEQUENCE: 4

```
Ile Tyr Ile Trp Ala Pro Leu Ala Gly Thr Cys Gly Val Leu Leu Leu
1               5                   10                  15

Ser Leu Val Ile Thr Leu Tyr Cys Lys
            20                  25
```

<210> SEQ ID NO 5
<211> LENGTH: 120
<212> TYPE: DNA
<213> ORGANISM: Artificial Sequence
<220> FEATURE:
<223> OTHER INFORMATION: 4-1BB co-stimulatory domain

<400> SEQUENCE: 5

```
cggggcagaa agaaactcct gtatatattc aacaaccat ttatgagacc agtacaaact     60
actcaagagg aagatggctg tagctgccga tttccagaag aagaagaagg aggatgtgaa   120
```

<210> SEQ ID NO 6
<211> LENGTH: 40
<212> TYPE: PRT
<213> ORGANISM: Artificial Sequence
<220> FEATURE:
<223> OTHER INFORMATION: 4-1BB co-stimulatory domain

<400> SEQUENCE: 6

```
Arg Gly Arg Lys Lys Leu Leu Tyr Ile Phe Lys Gln Pro Phe Met Arg
1               5                   10                  15

Pro Val Gln Thr Thr Gln Glu Glu Asp Gly Cys Ser Cys Arg Phe Pro
            20                  25                  30

Glu Glu Glu Glu Gly Gly Cys Glu
        35                  40
```

<210> SEQ ID NO 7
<211> LENGTH: 339
<212> TYPE: DNA
<213> ORGANISM: Artificial Sequence
<220> FEATURE:
<223> OTHER INFORMATION: CD3zeta signaling domain

<400> SEQUENCE: 7

```
ctgagagtga agttcagcag gagcgcagac gccccccgcgt accagcaggg ccagaaccag    60
ctctataacg agctcaatct aggacgaaga gaggagtacg atgttttgga caagagacgt   120
ggccgggacc ctgagatggg gggaaagccg agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg ccccctcgc                          339
```

-continued

```
<210> SEQ ID NO 8
<211> LENGTH: 113
<212> TYPE: PRT
<213> ORGANISM: Artificial Sequence
<220> FEATURE:
<223> OTHER INFORMATION: CD3zeta signaling domain

<400> SEQUENCE: 8

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 9
<211> LENGTH: 63
<212> TYPE: DNA
<213> ORGANISM: Artificial Sequence
<220> FEATURE:
<223> OTHER INFORMATION: CD8alpha signal peptide

<400> SEQUENCE: 9
atggccttac cagtgaccgc cttgctcctg ccgctggcct tgctgctcca cgccgccagg      60
ccg                                                                   63

<210> SEQ ID NO 10
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 10

Met Ala Leu Pro Val Thr Ala Leu Leu Leu Pro Leu Ala Leu Leu
1               5                   10                  15

His Ala Ala Arg Pro
            20

<210> SEQ ID NO 11
<211> LENGTH: 135
<212> TYPE: DNA
<213> ORGANISM: Artificial Sequence
<220> FEATURE:
<223> OTHER INFORMATION: CD8alpha hinge region

<400> SEQUENCE: 11
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat                                                     135
```

<210> SEQ ID NO 12
<211> LENGTH: 45
<212> TYPE: PRT
<213> ORGANISM: Artificial Sequence
<220> FEATURE:
<223> OTHER INFORMATION: CD8alpha hinge region

<400> SEQUENCE: 12

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 13
<211> LENGTH: 714
<212> TYPE: DNA
<213> ORGANISM: Artificial Sequence
<220> FEATURE:
<223> OTHER INFORMATION: mCD19 scFv

<400> SEQUENCE: 13

```
gacatccaga tgacccagag ccctgccagc ctgtctacca gcctgggcga gacagtgacc      60
atccagtgtc aggccagcga ggacatctac tctggcctgg cttggtatca gcagaagccc     120
ggcaagagcc ctcagctgct gatctacggc gccagcgacc tgcaggacgg cgtgcctagc     180
agattcagcg gcagcggctc cggaacccag tacagcctga gatcaccag catgcagacc      240 gaggacgagg gcgtgtactt ctgccagcaa ggcctgacct accctagaac cttcggagga     300
ggcaccaagc tggaactgaa gggcggaggc ggaagtggag gcggaggatc tggcggcgga     360
ggctctgaag tgcagctgca gcagtctggc gctgaactgg tccggcctgg cactagcgtg     420
aagctgtcct gcaaggtgtc cggcgacacc atcaccttct actacatgca cttcgtgaag     480
cagaggccag acagggcct ggaatggatc ggcagaatcg accctgagga cgagagcacc      540
aagtacagcg agaagttcaa gaacaaggcc accctgaccg ccgacaccag cagcaacacc     600
gcctacctga gctgtctag cctgacctcc gaggacaccg ccacctactt ttgcatctac      660
ggcggctact acttcgacta ctggggccag ggcgtgatgg tcaccgtgtc cagc           714
```

<210> SEQ ID NO 14
<211> LENGTH: 238
<212> TYPE: PRT
<213> ORGANISM: Artificial Sequence
<220> FEATURE:
<223> OTHER INFORMATION: mCD19 scFv

<400> SEQUENCE: 14

```
Asp Ile Gln Met Thr Gln Ser Pro Ala Ser Leu Ser Thr Ser Leu Gly
1               5                   10                  15

Glu Thr Val Thr Ile Gln Cys Gln Ala Ser Glu Asp Ile Tyr Ser Gly
            20                  25                  30

Leu Ala Trp Tyr Gln Gln Lys Pro Gly Lys Ser Pro Gln Leu Leu Ile
        35                  40                  45

Tyr Gly Ala Ser Asp Leu Gln Asp Gly Val Pro Ser Arg Phe Ser Gly
    50                  55                  60

Ser Gly Ser Gly Thr Gln Tyr Ser Leu Lys Ile Thr Ser Met Gln Thr
65                  70                  75                  80

Glu Asp Glu Gly Val Tyr Phe Cys Gln Gln Gly Leu Thr Tyr Pro Arg
                85                  90                  95
```

```
Thr Phe Gly Gly Gly Thr Lys Leu Glu Leu Lys Gly Gly Gly Gly Ser
            100                 105                 110
Gly Gly Gly Gly Ser Gly Gly Gly Ser Glu Val Gln Leu Gln Gln
        115                 120                 125
Ser Gly Ala Glu Leu Val Arg Pro Gly Thr Ser Val Lys Leu Ser Cys
    130                 135                 140
Lys Val Ser Gly Asp Thr Ile Thr Phe Tyr Tyr Met His Phe Val Lys
145                 150                 155                 160
Gln Arg Pro Gly Gln Gly Leu Glu Trp Ile Gly Arg Ile Asp Pro Glu
                165                 170                 175
Asp Glu Ser Thr Lys Tyr Ser Glu Lys Phe Lys Asn Lys Ala Thr Leu
            180                 185                 190
Thr Ala Asp Thr Ser Ser Asn Thr Ala Tyr Leu Lys Leu Ser Ser Leu
        195                 200                 205
Thr Ser Glu Asp Thr Ala Thr Tyr Phe Cys Ile Tyr Gly Gly Tyr Tyr
    210                 215                 220
Phe Asp Tyr Trp Gly Gln Gly Val Met Val Thr Val Ser Ser
225                 230                 235

<210> SEQ ID NO 15
<211> LENGTH: 63
<212> TYPE: DNA
<213> ORGANISM: Artificial Sequence
<220> FEATURE:
<223> OTHER INFORMATION: mCD8alpha transmembrane domain

<400> SEQUENCE: 15
atctgggcac ccttggccgg aatctgcgtg gcccttctgc tgtccttgat catcactctc      60
atc                                                                    63

<210> SEQ ID NO 16
<211> LENGTH: 21
<212> TYPE: PRT
<213> ORGANISM: Artificial Sequence
<220> FEATURE:
<223> OTHER INFORMATION: mCD8alpha transmembrane domain

<400> SEQUENCE: 16

Ile Trp Ala Pro Leu Ala Gly Ile Cys Val Ala Leu Leu Leu Ser Leu
1               5                   10                  15

Ile Ile Thr Leu Ile
            20

<210> SEQ ID NO 17
<211> LENGTH: 126
<212> TYPE: DNA
<213> ORGANISM: Artificial Sequence
<220> FEATURE:
<223> OTHER INFORMATION: m4-1BB co-stimulatory domain

<400> SEQUENCE: 17
aggaaaaaat tcccccacat attcaagcaa ccatttaaga gaccactgga agcagctcaa      60
gaggaagatg cttgtagctg ccgatgtcca caggaagaag aaggaggagg aggaggctat    120
gagctg                                                               126

<210> SEQ ID NO 18
<211> LENGTH: 42
<212> TYPE: PRT
<213> ORGANISM: Artificial Sequence
```

<220> FEATURE:
<223> OTHER INFORMATION: m4-1BB co-stimulatory domain

<400> SEQUENCE: 18

Arg Lys Lys Phe Pro His Ile Phe Lys Gln Pro Phe Lys Lys Thr Thr
1               5                   10                  15
Gly Ala Ala Gln Glu Glu Asp Ala Cys Ser Cys Arg Cys Pro Gln Glu
            20                  25                  30
Glu Glu Gly Gly Gly Gly Gly Tyr Glu Leu
        35                  40

<210> SEQ ID NO 19
<211> LENGTH: 327
<212> TYPE: DNA
<213> ORGANISM: Artificial Sequence
<220> FEATURE:
<223> OTHER INFORMATION: mCD3zeta intracellular signaling domain

<400> SEQUENCE: 19
agcaggagtg cagagactgc tgccaacctg caggacccca accagctcta caatgagctc      60
aatctagggc gaagagagga atatgacgtc ttggagaaga gcgggctcg ggatccagag      120 atgggaggca acagcagag gaggaggaac ccccaggaag gcgtatacaa tgcactgcag      180
aaagacaaga tggcagaagc ctacagtgag atcggcacaa aggcgagag gcggagaggc      240 aaggggcacg atggccttta ccagggtctc agcactgcca ccaaggacac ctatgatgcc      300
ctgcatatgc agaccctggc ccctcgc                                          327

<210> SEQ ID NO 20
<211> LENGTH: 109
<212> TYPE: PRT
<213> ORGANISM: Artificial Sequence
<220> FEATURE:
<223> OTHER INFORMATION: mCD3zeta intracellular signaling domain

<400> SEQUENCE: 20

Ser Arg Ser Ala Glu Thr Ala Ala Asn Leu Gln Asp Pro Asn Gln Leu
1               5                   10                  15
Tyr Asn Glu Leu Asn Leu Gly Arg Arg Glu Glu Tyr Asp Val Leu Glu
            20                  25                  30
Lys Lys Arg Ala Arg Asp Pro Glu Met Gly Gly Lys Gln Gln Arg Arg
        35                  40                  45
Arg Asn Pro Gln Glu Gly Val Tyr Asn Ala Leu Gln Lys Asp Lys Met
    50                  55                  60
Ala Glu Ala Tyr Ser Glu Ile Gly Thr Lys Gly Glu Arg Arg Arg Gly
65                  70                  75                  80
Lys Gly His Asp Gly Leu Tyr Gln Gly Leu Ser Thr Ala Thr Lys Asp
                85                  90                  95
Thr Tyr Asp Ala Leu His Met Gln Thr Leu Ala Pro Arg
            100                 105

<210> SEQ ID NO 21
<211> LENGTH: 135
<212> TYPE: DNA
<213> ORGANISM: Artificial Sequence
<220> FEATURE:
<223> OTHER INFORMATION: mCD8alpha hinge region

<400> SEQUENCE: 21
actactacca agccagtgct gcgaactccc tcacctgtgc accctaccgg gacatctcag      60

```
cccagagac cagaagattg tcggccccgt ggctcagtga aggggaccgg attggacttc    120
gcctgtgata tttac                                                     135
```

<210> SEQ ID NO 22
<211> LENGTH: 45
<212> TYPE: PRT
<213> ORGANISM: Artificial Sequence
<220> FEATURE:
<223> OTHER INFORMATION: mCD8alpha hinge region

<400> SEQUENCE: 22

```
Thr Thr Thr Lys Pro Val Leu Arg Thr Pro Ser Pro Val His Pro Thr
1               5                   10                  15

Gly Thr Ser Gln Pro Gln Arg Pro Glu Asp Cys Arg Pro Arg Gly Ser
            20                  25                  30

Val Lys Gly Thr Gly Leu Asp Phe Ala Cys Asp Ile Tyr
        35                  40                  45
```

<210> SEQ ID NO 23
<211> LENGTH: 402
<212> TYPE: DNA
<213> ORGANISM: Artificial Sequence
<220> FEATURE:
<223> OTHER INFORMATION: hIL-7

<400> SEQUENCE: 23

```
atgttccatg tttcttttag gtatatcttt ggacttcctc ccctgatcct tgttctgttg    60
ccagtagcat catctgattg tgatattgaa ggtaaagatg gcaaacaata tgagagtgtt   120
ctaatggtca gcatcgatca attattggac agcatgaaag aaattggtag caattgcctg   180
aataatgaat taacttttt taaaagacat atctgtgatg ctaataaggt taaaggaaga   240
aaaccagctg ccctgggtga agcccaacca acaaagagtt tggaagaaaa taatctttta   300
aaggaacaga aaaaactgaa tgacttgtgt ttcctaaaga gactattaca agagataaaa   360
acttgttgga ataaaatttt gatgggcact aaagaacact ga                      402
```

<210> SEQ ID NO 24
<211> LENGTH: 133
<212> TYPE: PRT
<213> ORGANISM: Artificial Sequence
<220> FEATURE:
<223> OTHER INFORMATION: hIL-7

<400> SEQUENCE: 24

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Val Lys Gly Arg
65                  70                  75                  80

Lys Pro Ala Ala Leu Gly Glu Ala Gln Pro Thr Lys Ser Leu Glu Glu
                85                  90                  95

Asn Lys Ser Leu Lys Glu Gln Lys Lys Leu Asn Asp Leu Cys Phe Leu
            100                 105                 110

Lys Arg Leu Leu Gln Glu Ile Lys Thr Cys Trp Asn Lys Ile Leu Met
```

115                 120                 125
Gly Thr Lys Glu His
    130

<210> SEQ ID NO 25
<211> LENGTH: 345
<212> TYPE: DNA
<213> ORGANISM: Artificial Sequence
<220> FEATURE:
<223> OTHER INFORMATION: hXCL-1

<400> SEQUENCE: 25
atgagacttc tcatcctggc cctccttggc atctgctctc tcactgcata cattgtggaa     60
ggtgtaggga gtgaagtctc agataagagg acctgtgtga gcctcactac ccagcgactg    120
ccggttagca gaatcaagac ctacaccatc acggaaggct ccttgagagc agtaattttt    180
attaccaaac gtggcctaaa agtctgtgct gatccacaag ccacgtgggt gagagacgtg    240
gtcaggagca tggacaggaa atccaacacc agaaataaca tgatccagac caagccaaca    300
ggaacccagc aatcgaccaa tacagctgtg accctgactg gctag                    345

<210> SEQ ID NO 26
<211> LENGTH: 114
<212> TYPE: PRT
<213> ORGANISM: Artificial Sequence
<220> FEATURE:
<223> OTHER INFORMATION: hXCL-1

<400> SEQUENCE: 26

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 27
<211> LENGTH: 465
<212> TYPE: DNA
<213> ORGANISM: Artificial Sequence
<220> FEATURE:
<223> OTHER INFORMATION: mIL-7

<400> SEQUENCE: 27
atgttccatg tttcttttag atatatcttt ggaattcctc cactgatcct tgttctgctg     60
cctgtcacat catctgagtg ccacattaaa gacaaagaag gtaaagcata tgagagtgta    120
ctgatgatca gcatcgatga attggacaaa atgacaggaa ctgatagtaa ttgcccgaat    180
aatgaaccaa acttttttag aaaacatgta tgtgatgata caaggaagc tgcttttcta    240 aatcgtgctg ctcgcaagtt gaagcaattt cttaaaatga atatcagtga agaattcaat    300

```
gtccacttac taacagtatc acaaggcaca caaacactgg tgaactgcac aagtaaggaa    360
gaaaaaaacg taaggaaca gaaaagaat gatgcatgtt tcctaaagag actactgaga     420
gaaataaaaa cttgttggaa taaaattttg aagggcagta tataa                   465
```

```
<210> SEQ ID NO 28
<211> LENGTH: 154
<212> TYPE: PRT
<213> ORGANISM: Artificial Sequence
<220> FEATURE:
<223> OTHER INFORMATION: mIL-7

<400> SEQUENCE: 28
```

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
    50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
        115                 120                 125

Lys Asn Asp Ala Cys Phe Leu Lys Arg Leu Leu Arg Glu Ile Lys Thr
    130                 135                 140

Cys Trp Asn Lys Ile Leu Lys Gly Ser Ile
145                 150

```
<210> SEQ ID NO 29
<211> LENGTH: 345
<212> TYPE: DNA
<213> ORGANISM: Artificial Sequence
<220> FEATURE:
<223> OTHER INFORMATION: mXCL-1

<400> SEQUENCE: 29
```

```
atgagacttc tcctcctgac tttcctggga gtctgctgcc tcaccccatg ggttgtggaa    60
ggtgtgggga ctgaagtcct agaagagagt agctgtgtga acttacaaac ccagcggctg   120
ccagttcaaa aaatcaagac ctatatcatc tgggaggggg ccatgagagc tgtaattttt   180
gtcaccaaac gaggactaaa aatttgtgct gatccagaag ccaaatgggt gaaagcagcg   240
atcaagactg tggatggcag ggccagtacc agaaagaaca tggctgaaac tgttcccaca   300
ggagcccaga ggtccaccag cacagcagta accctgactg ggtaa                   345
```

```
<210> SEQ ID NO 30
<211> LENGTH: 114
<212> TYPE: PRT
<213> ORGANISM: Artificial Sequence
<220> FEATURE:
<223> OTHER INFORMATION: mXCL-1

<400> SEQUENCE: 30
```

```
Met Arg Leu Leu Leu Leu Thr Phe Leu Gly Val Cys Cys Leu Thr Pro
1               5                   10                  15

Trp Val Val Glu Gly Val Gly Thr Glu Val Leu Glu Glu Ser Ser Cys
            20                  25                  30

Val Asn Leu Gln Thr Gln Arg Leu Pro Val Gln Lys Ile Lys Thr Tyr
        35                  40                  45

Ile Ile Trp Glu Gly Ala Met Arg Ala Val Ile Phe Val Thr Lys Arg
    50                  55                  60

Gly Leu Lys Ile Cys Ala Asp Pro Glu Ala Lys Trp Val Lys Ala Ala
65                  70                  75                  80

Ile Lys Thr Val Asp Gly Arg Ala Ser Thr Arg Lys Asn Met Ala Glu
            85                  90                  95

Thr Val Pro Thr Gly Ala Gln Arg Ser Thr Ser Thr Ala Val Thr Leu
            100                 105                 110

Thr Gly

<210> SEQ ID NO 31
<211> LENGTH: 54
<212> TYPE: DNA
<213> ORGANISM: Artificial Sequence
<220> FEATURE:
<223> OTHER INFORMATION: T2A

<400> SEQUENCE: 31
gagggcagag gaagtcttct aacatgcggt gacgtggagg agaatcccgg ccct        54

<210> SEQ ID NO 32
<211> LENGTH: 18
<212> TYPE: PRT
<213> ORGANISM: Artificial Sequence
<220> FEATURE:
<223> OTHER INFORMATION: T2A

<400> SEQUENCE: 32

Glu Gly Arg Gly Ser Leu Leu Thr Cys Gly Asp Val Glu Glu Asn Pro
1               5                   10                  15

Gly Pro

<210> SEQ ID NO 33
<211> LENGTH: 72
<212> TYPE: DNA
<213> ORGANISM: Artificial Sequence
<220> FEATURE:
<223> OTHER INFORMATION: mCD8alpha signal peptide

<400> SEQUENCE: 33
atggcctcac cgttgacccg ctttctgtcg ctgaacctgc tgctgctggg tgagtcgatt    60
atcctgggga gt                                                       72

<210> SEQ ID NO 34
<211> LENGTH: 24
<212> TYPE: PRT
<213> ORGANISM: Artificial Sequence
<220> FEATURE:
<223> OTHER INFORMATION: mCD8alpha signal peptide

<400> SEQUENCE: 34

Met Ala Ser Pro Leu Thr Arg Phe Leu Ser Leu Asn Leu Leu Leu Leu
1               5                   10                  15

Gly Glu Ser Ile Ile Leu Gly Ser
            20
```

<210> SEQ ID NO 35
<211> LENGTH: 708
<212> TYPE: DNA
<213> ORGANISM: Artificial Sequence
<220> FEATURE:
<223> OTHER INFORMATION: hFlt3L

<400> SEQUENCE: 35

```
atgacagtgc tggcgccagc ctggagccca acaacctatc tcctcctgct gctgctgctg    60
agctcgggac tcagtgggac ccaggactgc tccttccaac acagcccat ctcctccgac    120
ttcgctgtca aaatccgtga gctgtctgac tacctgcttc aagattaccc agtcaccgtg    180
gcctccaacc tgcaggacga ggagctctgc gggggcctct ggcggctggt cctggcacag    240
cgctggatgg agcggctcaa gactgtcgct gggtccaaga tgcaaggctt gctggagcgc    300
gtgaacacgg agatacactt tgtcaccaaa tgtgcctttc agccccccc cagctgtctt    360
cgcttcgtcc agaccaacat ctcccgcctc ctgcaggaga cctccgagca gctggtggcg    420
ctgaagccct ggatcactcg ccagaacttc tcccgtgcc tggagctgca gtgtcagccc    480
gactcctcaa ccctgccacc cccatggagt ccccggcccc tggaggccac agccccgaca    540
gccccgcagc cccctctgct cctcctactg ctgctgcccg tgggcctcct gctgctggcc    600
gctgctggt gcctgcactg cagaggacg cggcggagga cacccgccc tgggggagcag    660
gtgccccccg tccccagtcc ccaggacctg ctgcttgtgg agcactga                708
```

<210> SEQ ID NO 36
<211> LENGTH: 235
<212> TYPE: PRT
<213> ORGANISM: Artificial Sequence
<220> FEATURE:
<223> OTHER INFORMATION: hFlt3L

<400> SEQUENCE: 36

```
Met Thr Val Leu Ala Pro Ala Trp Ser Pro Thr Thr Tyr Leu Leu Leu
1               5                   10                  15

Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
```

```
                180             185                 190
Pro Val Gly Leu Leu Leu Ala Ala Ala Trp Cys Leu His Trp Gln
            195                 200             205

Arg Thr Arg Arg Arg Thr Pro Arg Pro Gly Glu Gln Val Pro Pro Val
        210                 215                 220

Pro Ser Pro Gln Asp Leu Leu Leu Val Glu His
225                 230                 235
```

<210> SEQ ID NO 37
<211> LENGTH: 699
<212> TYPE: DNA
<213> ORGANISM: Artificial Sequence
<220> FEATURE:
<223> OTHER INFORMATION: mFlt3L

<400> SEQUENCE: 37

```
atgacagtgc tggcgccagc ctggagccca aattcctccc tgttgctgct gttgctgctg      60
ctgagtcctt gcctgcgggg gacacctgac tgttacttca gccacagtcc catctcctcc     120
aacttcaaag tgaagtttag agagttgact gaccaccctg ttaaagatta cccagtcact     180
gtggccgtca tcttcaggac gagaagcac tgcaaggcct tgtggagcct cttcctagcc     240
cagcgctgga tagagcaact gaagactgtg cagggtctaa gatgcaaac gcttctggag     300
gacgtcaaca ccgagataca ttttgtcacc tcatgtacct ccagcccct accagaatgt     360
ctgcgattcg tccagaccaa catctcccac ctcctgaagg cacctgcac acagctgctt     420
gctctgaagc cctgtatcgg gaaggcctgc cagaatttct ctcggtgcct ggaggtgcag     480
tgccagccgg actcctccac cctgctgccc ccaaggagtc ccatagccct agaagccacg     540
gagctcccag agcctcggcc caggcagctg ttgctcctgc tgctgctgct gctgcctctc     600
acactggtgc tgctggcagc cgcctggggc cttcgctggc aaagggcaag aaggaggggg     660
gagctccacc ctggggtgcc cctcccctcc catccctag                             699
```

<210> SEQ ID NO 38
<211> LENGTH: 232
<212> TYPE: PRT
<213> ORGANISM: Artificial Sequence
<220> FEATURE:
<223> OTHER INFORMATION: mFlt3L

<400> SEQUENCE: 38

```
Met Thr Val Leu Ala Pro Ala Trp Ser Pro Asn Ser Ser Leu Leu Leu
1               5                   10                  15

Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
            35                  40                  45

Leu Thr Asp His Leu Leu Lys Asp Tyr Pro Val Thr Val Ala Val Asn
        50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
            115                 120                 125
```

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Leu Pro Leu Thr Leu Val Leu Leu Ala Ala Ala
            195                 200                 205

Trp Gly Leu Arg Trp Gln Arg Ala Arg Arg Arg Gly Glu Leu His Pro
    210                 215                 220

Gly Val Pro Leu Pro Ser His Pro
225                 230

<210> SEQ ID NO 39
<211> LENGTH: 660
<212> TYPE: DNA
<213> ORGANISM: Artificial Sequence
<220> FEATURE:
<223> OTHER INFORMATION: hIL-12

<400> SEQUENCE: 39
atgtgtccag cgcgcagcct cctccttgtg gctaccctgg tcctcctgga ccacctcagt       60
ttggccagaa acctccccgt ggccactcca gacccaggaa tgttcccatg ccttcaccac      120
tcccaaaacc tgctgagggc cgtcagcaac atgctccaga aggccagaca aactctagaa      180
ttttaccctt gcacttctga agagattgat catgaagata tcacaaaaga taaaaccagc      240
acagtggagg cctgtttacc attggaatta accaagaatg agagttgcct aaattccaga      300
gagacctctt catcaactaa tgggagttgc ctggcctcca aaagacctc tttatgatg       360 gccctgtgcc ttagtagtat ttatgaagac ttgaagatgt accaggtgga gttcaagacc      420
atgaatgcaa agcttctgat ggatcctaag aggcagatct ttctagatca aaacatgctg      480
gcagttattg atgagctgat gcaggccctg aatttcaaca gtgagactgt gccacaaaaa      540
tcctcccttg aagaaccgga ttttataaaa actaaaatca agctctgcat acttcttcat      600
gctttcagaa ttcgggcagt gactattgac agagtgacga gctatctgaa tgcttcctaa      660

<210> SEQ ID NO 40
<211> LENGTH: 219
<212> TYPE: PRT
<213> ORGANISM: Artificial Sequence
<220> FEATURE:
<223> OTHER INFORMATION: hIL-12

<400> SEQUENCE: 40

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys 85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Thr Ser Tyr Leu Asn Ala Ser
    210                 215

<210> SEQ ID NO 41
<211> LENGTH: 648
<212> TYPE: DNA
<213> ORGANISM: Artificial Sequence
<220> FEATURE:
<223> OTHER INFORMATION: mIL-12

<400> SEQUENCE: 41
atgtgtcaat cacgctacct cctcttttg gccaccttg ccctcctaaa ccacctcagt      60
ttggccaggg tcattccagt ctctggacct gccaggtgtc ttagccagtc ccgaaacctg   120
ctgaagacca cagatgacat ggtgaagacg gccagagaaa aactgaaaca ttattcctgc   180
actgctgaag acatcgatca tgaagacatc acacgggacc aaaccagcac attgaagacc   240
tgtttaccac tggaactaca caagaacgag agttgcctgg ctactagaga gacttcttcc   300
acaacaagag ggagctgcct gccccccacag aagacgtctt tgatgatgac cctgtgcctt   360
ggtagcatct atgaggactt gaagatgtac cagacagagt ccaggccat caacgcagca   420 cttcagaatc acaaccatca gcagatcatt ctagacaagg gcatgctggt ggccatcgat   480
gagctgatgc agtctctgaa tcataatggc gagactctgc cccagaaacc tcctgtggga   540
gaagcagacc cttacagagt gaaaatgaag ctctgcatcc tgcttcacgc cttcagcacc   600
cgcgtcgtga ccatcaacag ggtgatgggc tatctgagct ccgcctga              648

<210> SEQ ID NO 42
<211> LENGTH: 215
<212> TYPE: PRT
<213> ORGANISM: Artificial Sequence
<220> FEATURE:
<223> OTHER INFORMATION: mIL-12

<400> SEQUENCE: 42

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215

<210> SEQ ID NO 43
<211> LENGTH: 462
<212> TYPE: DNA
<213> ORGANISM: Artificial Sequence
<220> FEATURE:
<223> OTHER INFORMATION: hIL-2

<400> SEQUENCE: 43
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat acaagaatc ccaaactcac caggatgctc      180
acatttaagt tttacatgcc caagaaggcc acagaactga acatcttca gtgtctagaa      240 gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                       462

<210> SEQ ID NO 44
<211> LENGTH: 153
<212> TYPE: PRT
<213> ORGANISM: Artificial Sequence
<220> FEATURE:
<223> OTHER INFORMATION: hIL-2

<400> SEQUENCE: 44

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 45
<211> LENGTH: 510
<212> TYPE: DNA
<213> ORGANISM: Artificial Sequence
<220> FEATURE:
<223> OTHER INFORMATION: mIL-2

<400> SEQUENCE: 45
atgtacagca tgcagctcgc atcctgtgtc acattgacac ttgtgctcct tgtcaacagc        60
gcacccactt caagctccac ttcaagctct acagcggaag cacagcagca gcagcagcag       120
cagcagcagc agcagcagca cctggagcag ctgttgatgg acctacagga gctcctgagc       180
aggatggaga attacaggaa cctgaaactc cccaggatgc tcaccttcaa attttacttg       240
cccaagcagg ccacagaatt gaaagatctt cagtgcctag aagatgaact tggacctctg       300
cggcatgttc tggatttgac tcaaagcaaa agctttcaat ggaagatgc tgagaatttc        360 atcagcaata tcagagtaac tgttgtaaaa ctaaagggct ctgacaacac atttgagtgc       420
caattcgatg atgagtcagc aactgtggtg gactttctga ggagatggat agccttctgt       480
caaagcatca tctcaacaag ccctcaataa                                        510

<210> SEQ ID NO 46
<211> LENGTH: 169
<212> TYPE: PRT
<213> ORGANISM: Artificial Sequence
<220> FEATURE:
<223> OTHER INFORMATION: mIL-2

<400> SEQUENCE: 46

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
        50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

```
Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 47
<211> LENGTH: 408
<212> TYPE: DNA
<213> ORGANISM: Artificial Sequence
<220> FEATURE:
<223> OTHER INFORMATION: hIL-15

<400> SEQUENCE: 47
atggtattgg gaaccataga tttgtgcagc tgtttcagtg cagggcttcc taaaacagaa      60
gccaactggg tgaatgtaat aagtgatttg aaaaaaattg aagatcttat tcaatctatg     120
catattgatg ctactttata tacgaaaagt gatgttcacc ccagttgcaa agtaacagca     180
atgaagtgct ttctcttgga gttacaagtt atttcacttg agtccggaga tgcaagtatt     240
catgatacag tagaaaatct gatcatccta gcaacaacaa gtttgtcttc taatgggaat     300
gtaacagaat ctggatgcaa agaatgtgag gaactggagg aaaaaaatat taagaatttt     360
ttgcagagtt ttgtacatat tgtccaaatg ttcatcaaca cttcttga                  408

<210> SEQ ID NO 48
<211> LENGTH: 135
<212> TYPE: PRT
<213> ORGANISM: Artificial Sequence
<220> FEATURE:
<223> OTHER INFORMATION: hIL-15

<400> SEQUENCE: 48

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 49
<211> LENGTH: 489
<212> TYPE: DNA
<213> ORGANISM: Artificial Sequence
<220> FEATURE:
<223> OTHER INFORMATION: mIL-15
```

<400> SEQUENCE: 49

```
atgaaaattt tgaaaccata tatgaggaat acatccatct cgtgctactt gtgtttcctt    60
ctaaacagtc acttttaac tgaggctggc attcatgtct tcattttggg ctgtgtcagt   120
gtaggtctcc ctaaaacaga ggccaactgg atagatgtaa gatatgacct ggagaaaatt   180
gaaagcctta ttcaatctat tcatattgac accactttat acactgacag tgactttcat   240
cccagttgca agttactgc aatgaactgc tttctcctgg aattgcaggt tattttacat   300
gagtacagta acatgactct taatgaaaca gtaagaaacg tgctctacct tgcaaacagc   360
actctgtctt ctaacaagaa tgtagcagaa tctggctgca aggaatgtga ggagctggag   420
gagaaaacct tcacagagtt tttgcaaagc tttatacgca ttgtccaaat gttcatcaac   480
acgtcctga                                                           489
```

<210> SEQ ID NO 50
<211> LENGTH: 162
<212> TYPE: PRT
<213> ORGANISM: Artificial Sequence
<220> FEATURE:
<223> OTHER INFORMATION: mIL-15

<400> SEQUENCE: 50

```
Met Lys Ile Leu Lys Pro Tyr Met Arg Asn Thr Ser Ile Ser Cys Tyr
1               5                   10                  15
Leu Cys Phe Leu Leu Asn Ser His Phe Leu Thr Glu Ala Gly Ile His
            20                  25                  30
Val Phe Ile Leu Gly Cys Val Ser Val Gly Leu Pro Lys Thr Glu Ala
        35                  40                  45
Asn Trp Ile Asp Val Arg Tyr Asp Leu Glu Lys Ile Glu Ser Leu Ile
    50                  55                  60
Gln Ser Ile His Ile Asp Thr Thr Leu Tyr Thr Asp Ser Asp Phe His
65                  70                  75                  80
Pro Ser Cys Lys Val Thr Ala Met Asn Cys Phe Leu Leu Glu Leu Gln
                85                  90                  95
Val Ile Leu His Glu Tyr Ser Asn Met Thr Leu Asn Glu Thr Val Arg
            100                 105                 110
Asn Val Leu Tyr Leu Ala Asn Ser Thr Leu Ser Ser Asn Lys Asn Val
        115                 120                 125
Ala Glu Ser Gly Cys Lys Glu Cys Glu Glu Leu Glu Glu Lys Thr Phe
    130                 135                 140
Thr Glu Phe Leu Gln Ser Phe Ile Arg Ile Val Gln Met Phe Ile Asn
145                 150                 155                 160
Thr Ser
```

<210> SEQ ID NO 51
<211> LENGTH: 489
<212> TYPE: DNA
<213> ORGANISM: Artificial Sequence
<220> FEATURE:
<223> OTHER INFORMATION: hIL-21

<400> SEQUENCE: 51

```
atgagatcca gtcctggcaa catggagagg attgtcatct gtctgatggt catcttcttg    60
gggacactgg tccacaaatc aagctcccaa ggtcaagatc gccacatgat tagaatgcgt   120
caacttatag atattgttga tcagctgaaa aattatgtga atgacttggt ccctgaattt   180
ctgccagctc cagaagatgt agagacaaac tgtgagtggt cagcttttc ctgttttcag   240
```

```
aaggcccaac taaagtcagc aaatacagga acaatgaaa ggataatcaa tgtatcaatt      300
aaaaagctga agaggaaacc accttccaca atgcaggga gaagacagaa acacagacta      360 acatgcccctt catgtgattc ttatgagaaa aaaccaccca agaattcct agaaagattc     420 aaatcacttc tccaaaagat gattcatcag catctgtcct ctagaacaca cggaagtgaa     480
gattcctga                                                             489
```

<210> SEQ ID NO 52
<211> LENGTH: 162
<212> TYPE: PRT
<213> ORGANISM: Artificial Sequence
<220> FEATURE:
<223> OTHER INFORMATION: hIL-21

<400> SEQUENCE: 52

```
Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser
```

<210> SEQ ID NO 53
<211> LENGTH: 441
<212> TYPE: DNA
<213> ORGANISM: Artificial Sequence
<220> FEATURE:
<223> OTHER INFORMATION: mIL-21

<400> SEQUENCE: 53

```
atggagagga cccttgtctg tctggtagtc atcttcttgg ggacagtggc ccataaatca      60
agcccccaag ggccagatcg cctcctgatt agacttcgtc accttattga cattgttgaa     120
cagctgaaaa tctatgaaaa tgacttggat cctgaacttc tatcagctcc acaagatgta     180
aaggggcact gtgagcatgc agcttttgcc tgttttcaga aggccaaact caagccatca     240
aaccctggaa acaataagac attcatcatt gacctcgtgg cccagctcag gaggaggctg     300
cctgccagga ggggaggaaa gaaacagaag cacatagcta atgcccttc ctgtgattcg      360 tatgagaaaa ggacacccaa agaattccta gaaagactaa atggctcct tcaaaagatg     420 attcatcagc atctctccta g                                               441
```

<210> SEQ ID NO 54
<211> LENGTH: 146
<212> TYPE: PRT
<213> ORGANISM: Artificial Sequence
<220> FEATURE:
<223> OTHER INFORMATION: mIL-21

<400> SEQUENCE: 54

```
Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145
```

<210> SEQ ID NO 55
<211> LENGTH: 468
<212> TYPE: DNA
<213> ORGANISM: Artificial Sequence
<220> FEATURE:
<223> OTHER INFORMATION: hIL-17

<400> SEQUENCE: 55

```
atgactcctg ggaagaccct cattggtgtca ctgctactgc tgctgagcct ggaggccata      60
gtgaaggcag gaatcacaat cccacgaaat ccaggatgcc caaattctga ggacaagaac     120
ttcccccgga ctgtgatggt caacctgaac atccataacc ggaataccaa taccaatccc     180
aaaaggtcct cagattacta caaccgatcc acctcacctt ggaatctcca ccgcaatgag     240
gaccctgaga gatatccctc tgtgatctgg gaggcaaagt gccgccactt gggctgcatc     300
aacgctgatg ggaacgtgga ctaccacatg aactctgtcc ccatccagca agagatcctg     360
gtcctgcgca gggagcctcc acactgcccc aactccttcc ggctggagaa gatactggtg     420
tccgtgggct gcacctgtgt caccccgatt gtccaccatg tggcctaa                  468
```

<210> SEQ ID NO 56
<211> LENGTH: 155
<212> TYPE: PRT
<213> ORGANISM: Artificial Sequence
<220> FEATURE:
<223> OTHER INFORMATION: hIL-17

<400> SEQUENCE: 56

```
Met Thr Pro Gly Lys Thr Ser Leu Val Ser Leu Leu Leu Leu Leu Ser
1               5                   10                  15
```

```
Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
                35                  40                  45

Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
                115                 120                 125

Cys Pro Asn Ser Phe Arg Leu Glu Lys Ile Leu Val Ser Val Gly Cys
                130                 135                 140

Thr Cys Val Thr Pro Ile Val His His Val Ala
145                 150                 155
```

<210> SEQ ID NO 57
<211> LENGTH: 477
<212> TYPE: DNA
<213> ORGANISM: Artificial Sequence
<220> FEATURE:
<223> OTHER INFORMATION: mIL-17

<400> SEQUENCE: 57

```
atgagtccag ggagagcttc atctgtgtct ctgatgctgt tgctgctgct gagcctggcg      60
gctacagtga aggcagcagc gatcatccct caaagctcag cgtgtccaaa cactgaggcc     120
aaggacttcc tccagaatgt gaaggtcaac ctcaaagtct ttaactccct tggcgcaaaa     180
gtgagctcca gaaggccctc agactacctc aaccgttcca cgtcaccctg gactctccac     240
cgcaatgaag accctgatag atatccctct gtgatctggg aagctcagtg ccgccaccag     300
cgctgtgtca tgcgcgaggg aaagctggac caccacatga attctgttct catccagcaa     360
gagatcctgg tcctgaagag ggagcctgag agctgccccct tcactttcag ggtcgagaag     420
atgctggtgg gtgtgggctg cacctgcgtg gcctcgattg tccgccaggc agcctaa       477
```

<210> SEQ ID NO 58
<211> LENGTH: 158
<212> TYPE: PRT
<213> ORGANISM: Artificial Sequence
<220> FEATURE:
<223> OTHER INFORMATION: mIL-17

<400> SEQUENCE: 58

```
Met Ser Pro Gly Arg Ala Ser Ser Val Ser Leu Met Leu Leu Leu Leu
 1               5                  10                  15

Leu Ser Leu Ala Ala Thr Val Lys Ala Ala Ala Ile Ile Pro Gln Ser
            20                  25                  30

Ser Ala Cys Pro Asn Thr Glu Ala Lys Asp Phe Leu Gln Asn Val Lys
            35                  40                  45

Val Asn Leu Lys Val Phe Asn Ser Leu Gly Ala Lys Val Ser Ser Arg
 50                  55                  60

Arg Pro Ser Asp Tyr Leu Asn Arg Ser Thr Ser Pro Trp Thr Leu His
 65                  70                  75                  80

Arg Asn Glu Asp Pro Asp Arg Tyr Pro Ser Val Ile Trp Glu Ala Gln
```

```
                85                  90                  95
Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
            115                 120                 125

Pro Glu Ser Cys Pro Phe Thr Phe Arg Val Glu Lys Met Leu Val Gly
130                 135                 140

Val Gly Cys Thr Cys Val Ala Ser Ile Val Arg Gln Ala Ala
145                 150                 155

<210> SEQ ID NO 59
<211> LENGTH: 582
<212> TYPE: DNA
<213> ORGANISM: Artificial Sequence
<220> FEATURE:
<223> OTHER INFORMATION: hIL-18

<400> SEQUENCE: 59
atggctgctg aaccagtaga agacaattgc atcaactttg tggcaatgaa atttattgac      60
aatacgcttt actttatagc tgaagatgat gaaaacctgg aatcagatta ctttggcaag    120
cttgaatcta aattatcagt cataagaaat ttgaatgacc aagttctctt cattgaccaa    180
ggaaatcggc ctctatttga agatatgact gattctgact gtagagataa tgcaccccgg    240
accatattta ttataagtat gtataaagat agccagccta gaggtatggc tgtaactatc    300
tctgtgaagt gtgagaaaat ttcaactctc tcctgtgaga acaaaattat tccctttaag    360
gaaatgaatc ctcctgataa catcaaggat acaaaaagtg acatcatatt ctttcagaga    420
agtgtcccag acatgataa taagatgcaa tttgaatctt catcatacga aggatacttt    480
ctagcttgtg aaaagagag agaccttttt aaactcattt tgaaaaaga ggatgaattg     540 ggggatagat ctataatgtt cactgttcaa aacgaagact ag                       582

<210> SEQ ID NO 60
<211> LENGTH: 193
<212> TYPE: PRT
<213> ORGANISM: Artificial Sequence
<220> FEATURE:
<223> OTHER INFORMATION: hIL-18

<400> SEQUENCE: 60

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
```

```
                130                 135                 140
His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 61
<211> LENGTH: 579
<212> TYPE: DNA
<213> ORGANISM: Artificial Sequence
<220> FEATURE:
<223> OTHER INFORMATION: mIL-18

<400> SEQUENCE: 61
atggctgcca tgtcagaaga ctcttgcgtc aacttcaagg aaatgatgtt tattgacaac      60
acgctttact ttatacctga agaaatgga gacctggaat cagacaactt tggccgactt     120
cactgtacaa ccgcagtaat acggaatata aatgaccaag ttctcttcgt tgacaaaaga     180
cagcctgtgt tcgaggatat gactgatatt gatcaaagtg ccagtgaacc ccagaccaga     240
ctgataatat acatgtacaa agacagtgaa gtaagaggac tggctgtgac cctctctgtg     300
aaggatagta aatgtctac cctctcctgt aagaacaaga tcatttcctt tgaggaaatg     360
gatccacctg aaaatattga tgatatacaa agtgatctca tattctttca gaaacgtgtt     420
ccaggacaca caagatgga gtttgaatct tcactgtatg aaggacactt tcttgcttgc     480
caaaaggaag atgatgcttt caaactcatt ctgaaaaaaa aggatgaaaa tggggataaa     540
tctgtaatgt tcactctcac taacttacat caaagttag                           579

<210> SEQ ID NO 62
<211> LENGTH: 192
<212> TYPE: PRT
<213> ORGANISM: Artificial Sequence
<220> FEATURE:
<223> OTHER INFORMATION: mIL-18

<400> SEQUENCE: 62

Met Ala Ala Met Ser Glu Asp Ser Cys Val Asn Phe Lys Glu Met Met
1               5                   10                  15

Phe Ile Asp Asn Thr Leu Tyr Phe Ile Pro Glu Glu Asn Gly Asp Leu
            20                  25                  30

Glu Ser Asp Asn Phe Gly Arg Leu His Cys Thr Thr Ala Val Ile Arg
        35                  40                  45

Asn Ile Asn Asp Gln Val Leu Phe Val Asp Lys Arg Gln Pro Val Phe
    50                  55                  60

Glu Asp Met Thr Asp Ile Asp Gln Ser Ala Ser Glu Pro Gln Thr Arg
65                  70                  75                  80

Leu Ile Ile Tyr Met Tyr Lys Asp Ser Glu Val Arg Gly Leu Ala Val
                85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
        115                 120                 125

Ile Gln Ser Asp Leu Ile Phe Phe Gln Lys Arg Val Pro Gly His Asn
    130                 135                 140
```

Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
                165                 170                 175

Asn Gly Asp Lys Ser Val Met Phe Thr Leu Thr Asn Leu His Gln Ser
            180                 185                 190

<210> SEQ ID NO 63
<211> LENGTH: 570
<212> TYPE: DNA
<213> ORGANISM: Artificial Sequence
<220> FEATURE:
<223> OTHER INFORMATION: hIL-23

<400> SEQUENCE: 63
atgctgggga gcagagctgt aatgctgctg ttgctgctgc cctggacagc tcagggcaga      60
gctgtgcctg ggggcagcag ccctgcctgg actcagtgcc agcagctttc acagaagctc     120
tgcacactgg cctggagtgc acatccacta gtgggacaca tggatctaag agaagaggga     180
gatgaagaga ctacaaatga tgttccccat atccagtgtg gagatggctg tgaccccaa      240 ggactcaggg acaacagtca gttctgcttg caaaggatcc accagggtct gattttttat     300
gagaagctgc taggatcgga tatttttcaca ggggagcctt ctctgctccc tgatagccct     360
gtggcgcagc ttcatgcctc cctactgggc tcagccaac cctgcagcc tgagggtcac       420 cactgggaga ctcagcagat tccaagcctc agtcccagcc agccatggca gcgtctcctt     480
ctccgcttca aaatccttcg cagcctccag gcctttgtgg ctgtagccgc ccgggtcttt      540
gcccatggag cagcaaccct gagtccctaa                                       570

<210> SEQ ID NO 64
<211> LENGTH: 189
<212> TYPE: PRT
<213> ORGANISM: Artificial Sequence
<220> FEATURE:
<223> OTHER INFORMATION: hIL-23

<400> SEQUENCE: 64

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Ala Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 65
<211> LENGTH: 591
<212> TYPE: DNA
<213> ORGANISM: Artificial Sequence
<220> FEATURE:
<223> OTHER INFORMATION: mIL-23

<400> SEQUENCE: 65

```
atgctggatt gcagagcagt aataatgcta tggctgttgc cctgggtcac tcagggcctg    60
gctgtgccta ggagtagcag tcctgactgg gctcagtgcc agcagctctc tcggaatctc   120
tgcatgctag cctggaacgc acatgcacca gcgggacata tgaatctact aagagaagaa   180
gaggatgaag agactaaaaa taatgtgccc cgtatccagt gtgaagatgg ttgtgaccca   240
caaggactca aggacaacag ccagttctgc ttgcaaagga tccgccaagg tctggctttt   300
tataagcacc tgcttgactc tgacatcttc aaagggagc ctgctctact ccctgatagc   360
cccatggagc aacttcacac ctccctacta ggactcagcc aactcctcca gccagaggat   420
caccccggg agacccaaca gatgcccagc ctgagttcta gtcagcagtg gcagcgcccc   480
cttctccgtt ccaagatcct cgaagcctc caggcctttt tggccatagc tgcccgggtc   540
tttgcccacg gagcagcaac tctgactgag cccttagtgc aacagctta               591
```

<210> SEQ ID NO 66
<211> LENGTH: 196
<212> TYPE: PRT
<213> ORGANISM: Artificial Sequence
<220> FEATURE:
<223> OTHER INFORMATION: mIL-23

<400> SEQUENCE: 66

Met Leu Asp Cys Arg Ala Val Ile Met Leu Trp Leu Leu Pro Trp Val
1               5                   10                  15

Thr Gln Gly Leu Ala Val Pro Arg Ser Ser Pro Asp Trp Ala Gln
            20                  25                  30

Cys Gln Gln Leu Ser Arg Asn Leu Cys Met Leu Ala Trp Asn Ala His
        35                  40                  45

Ala Pro Ala Gly His Met Asn Leu Leu Arg Glu Glu Asp Glu Glu
    50                  55                  60

Thr Lys Asn Asn Val Pro Arg Ile Gln Cys Glu Asp Gly Cys Asp Pro
65                  70                  75                  80

Gln Gly Leu Lys Asp Asn Ser Gln Phe Cys Leu Gln Arg Ile Arg Gln
                85                  90                  95

Gly Leu Ala Phe Tyr Lys His Leu Leu Asp Ser Asp Ile Phe Lys Gly
            100                 105                 110

Glu Pro Ala Leu Leu Pro Asp Ser Pro Met Glu Gln Leu His Thr Ser
        115                 120                 125

Leu Leu Gly Leu Ser Gln Leu Leu Gln Pro Glu Asp His Pro Arg Glu
    130                 135                 140

Thr Gln Gln Met Pro Ser Leu Ser Ser Gln Gln Trp Gln Arg Pro
145                 150                 155                 160

Leu Leu Arg Ser Lys Ile Leu Arg Ser Leu Gln Ala Phe Leu Ala Ile
                165                 170                 175

```
Ala Ala Arg Val Phe Ala His Gly Ala Ala Thr Leu Thr Glu Pro Leu
            180                 185                 190

Val Pro Thr Ala
        195

<210> SEQ ID NO 67
<211> LENGTH: 345
<212> TYPE: DNA
<213> ORGANISM: Artificial Sequence
<220> FEATURE:
<223> OTHER INFORMATION: hXCL2

<400> SEQUENCE: 67
atgagacttc tcatcctggc cctccttggc atctgctctc tcactgcata cattgtggaa      60
ggtgtaggga gtgaagtctc acataggagg acctgtgtga gcctcactac ccagcgactg     120
ccagttagca gaatcaagac ctacaccatc acggaaggct ccttgagagc agtaattttt     180
attaccaaac gtggcctaaa agtctgtgct gatccacaag ccacgtgggt gagagacgtg     240
gtcaggagca tggacaggaa atccaacacc agaaataaca tgatccagac caagccaaca     300
ggaacccagc aatcgaccaa tacagctgtg accctgactg gctag                     345

<210> SEQ ID NO 68
<211> LENGTH: 114
<212> TYPE: PRT
<213> ORGANISM: Artificial Sequence
<220> FEATURE:
<223> OTHER INFORMATION: hXCL2

<400> SEQUENCE: 68

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser His Arg Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
            85                  90                  95

Thr Lys Pro Thr Gly Thr Gln Gln Ser Thr Asn Thr Ala Val Thr Leu
            100                 105                 110

Thr Gly
```